(12) United States Patent
Sun

(10) Patent No.: US 7,729,870 B2
(45) Date of Patent: Jun. 1, 2010

(54) METHODS FOR DETECTING OIL DETERIORATION AND OIL LEVEL

(76) Inventor: Yizhong Sun, 30152 Galbreth Ct., Castaic, CA (US) 91384

( * ) Notice: Subject to any disclaimer, the term of this patent is extended or adjusted under 35 U.S.C. 154(b) by 216 days.

(21) Appl. No.: 11/899,320

(22) Filed: Sep. 5, 2007

(65) Prior Publication Data

US 2009/0063060 A1    Mar. 5, 2009

(51) Int. Cl.
*G06F 23/26*   (2006.01)
*G01N 11/00*   (2006.01)
(52) U.S. Cl. .................. 702/52; 73/53.05; 324/441; 324/698; 702/130
(58) Field of Classification Search ............. 702/50–52, 702/55, 57, 64, 100, 130; 701/30; 324/441, 324/698; 340/438, 439, 450.3, 603; 184/103.2; 73/53.05, 61.43
See application file for complete search history.

(56) References Cited

U.S. PATENT DOCUMENTS

| | | | |
|---|---|---|---|
| 4,517,547 A | 5/1985 | Gray | |
| 4,646,070 A | 2/1987 | Yasuhara et al. | |
| 4,733,556 A | 3/1988 | Meitzler et al. | |
| 4,764,258 A | 8/1988 | Kauffman | |
| 5,377,531 A | 1/1995 | Gomm | |
| 5,540,086 A | 7/1996 | Park et al. | |
| 5,929,754 A | 7/1999 | Park et al. | |
| 6,014,894 A | 1/2000 | Herron | |
| 6,278,281 B1 | 8/2001 | Bauer et al. | |
| 6,278,282 B1 | 8/2001 | Marszalek et al. | |
| 6,297,733 B1 | 10/2001 | Park et al. | |
| 6,535,001 B1 | 3/2003 | Wang | |
| 6,577,112 B2 | 6/2003 | Lvovich et al. | |
| 6,590,402 B2 | 7/2003 | Wang et al. | |
| 6,718,819 B2 | 4/2004 | Schoess | |
| 6,917,865 B2 | 7/2005 | Arai et al. | |
| 7,143,867 B2 | 12/2006 | Chopra | |
| 2006/0114007 A1 | 6/2006 | Cho | |
| 2006/0232267 A1 | 10/2006 | Halalay et al. | |

FOREIGN PATENT DOCUMENTS

CN         03140986.5         12/2003

*Primary Examiner*—John H Le

(57) ABSTRACT

Methods for detecting oil conditions including a top level of an oil in an oil system which is reduced to a top level of a predetermined threshold amount of the oil, a normal oil deterioration which occurs in the absence of water having a confirmed actual remaining usage of the oil, and an abnormal oil deterioration which occurs in the presence of water. The methods include a first preferred embodiment which applies reference and sensing capacitors to obtain a measured temperature compensated electrical property of the oil. From which a quantitatively measured remaining usage is obtained so as to a predicted one for the oil. Therefore, the respective top oil level, or the normal or the abnormal oil deterioration can be concluded according to the measured remaining usage which is respectively larger than, or similar to, or less than the predicted one for the oil. A second preferred embodiment only includes the sensing capacitor for obtaining the measured temperature compensated electrical property of the oil. Variations to the embodiments lead to application of at least two sensing capacitors to monitor an uneven distribution of the oil deterioration or a full range of the level of the oil in the entire oil system.

28 Claims, 11 Drawing Sheets

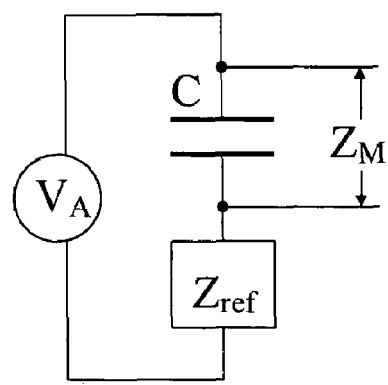 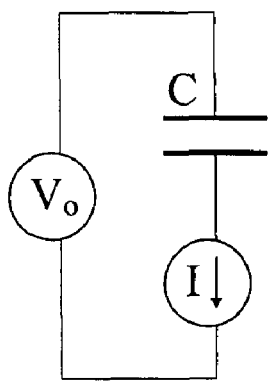 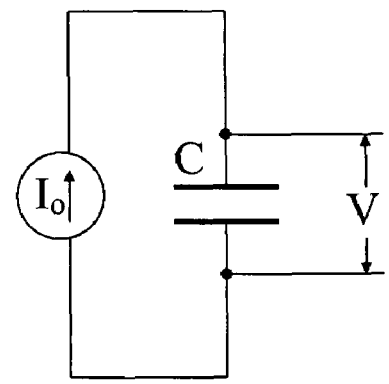
FIG. 5         FIG. 6         FIG. 7
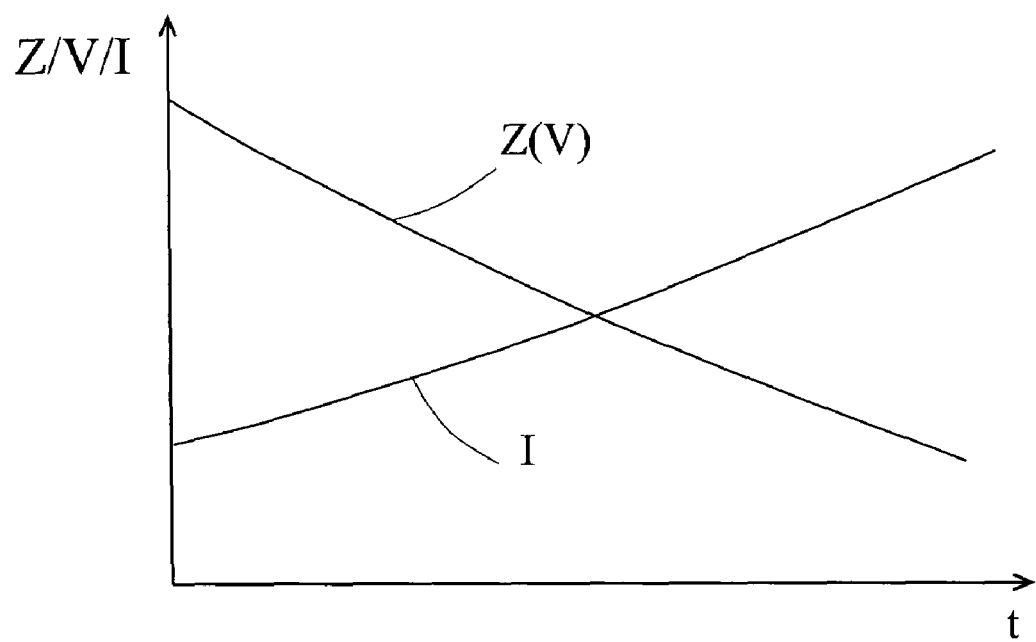
FIG. 8

METHODS FOR DETECTING OIL DETERIORATION AND OIL LEVEL

BACKGROUND OF INVENTION

1. Field of the Invention

The present invention is generally related to oil which is used in machinery such as internal combustion engines and electrical transformers, and more particularly related to methods for the on-line detection of the oil level, and the oil deterioration which occurs in the presence or absence of water.

2. Description of the Prior Art

Devices and methods for detecting oil deterioration and oil level are well known. The following 20 patents and published patent applications are the closest prior art references which are related to the present invention.

1. U.S. Pat. No. 4,517,547 issued to Gary et al. on May 14, 1985 for "Water-In-Fuel Sensor Circuit And Method" (hereafter the "Gary Patent");
2. U.S. Pat. No. 4,646,070 issued to Yasuhara et al. on Feb. 24, 1987 for "Oil Deterioration Detector Method And Apparatus" (hereafter the "Yasuhara Patent");
3. U.S. Pat. No. 4,764,258 issued to Kauffman on Aug. 16, 1988 for "Method For Evaluating The Remaining Useful Life Of A Hydrocarbon Oil" (hereafter the "Kauffman Patent");
4. U.S. Pat. No. 5,540,086 issued to Park et al. on Jul. 30, 1996 for "Oil Deterioration Sensor" (hereafter the "Park First Patent");
5. U.S. Pat. No. 5,929,754 issued to Park, et al. on Jul. 27, 1999 for "High Sensitivity Capacitive Oil Deterioration and Level Sensor" (hereafter the "Park Second Patent");
6. U.S. Pat. No. 6,297,733 issued to Park, et al. on Oct. 2, 2001 for "Stable, Reliable Capacitive Oil Deterioration And Level Sensor" (hereafter the "Park Third Patent");
7. U.S. Pat. No. 5,377,531 issued to Gomn on Jan. 3, 1995 for "Portable Oil Change Analyzer" (hereafter the "Gomn Patent");
8. U.S. Pat. No. 4,733,556 issued to Meitzler et al. on Mar. 29, 1988 for "Method And Apparatus For Sensing The Condition of Lubricating Oil In An Internal Combustion Engine" (hereafter the "Meitzler Patent");
9. U.S. Pat. No. 6,278,282 issued to Marszalek on Aug. 21, 2001 for "Method And System For Determining Oil Quality" (hereafter the "Marszalek Patent");
10. U.S. Pat. No. 6,590,402 issued to Wang et al. on Jul. 8, 2003 for "Engine Oil Condition Sensor" (hereafter the "Wang First Patent");
11. U.S. Pat. No. 6,535,001 issued to Wang on Mar. 18, 2003 for "Method and device For Sensing Oil Condition" (hereafter the "Wang Second Patent");
12. U.S. Pat. No. 6,577,112 issued to Lvovich et al. on Jun. 10, 2003 for "Method And Apparatus For On-Line Monitoring Of Quality And/Or Condition of High Resistive Fluids" (hereafter the "Lvovich Patent");
13. U.S. Pat. No. 7,143,867 issued to Chopra on Dec. 5, 2006 for "Electronic Oil Level Detection And Replacement System" (hereafter the "Chopra Patent");
14. United States Patent Application Publication No.: 2006/0232267 issued to Halalay et al. on Oct. 19, 2006 for "Determining Quality Of Lubricating Oils In Use" (hereafter the "Halalay Publication");
15. U.S. Pat. No. 6,718,819 issued to Schoess on Apr. 13, 2004 for "Oil Quality Sensor System, Method and Apparatus" (hereafter the "Schoess Patent");
16. U.S. Pat. No. 6,278,281 issued to Bauer et al. on Aug. 21, 2001 for "Fluid Condition Monitor" (hereafter the "Bauer Patent");
17. U.S. Pat. No. 6,014,894 issued to Herron on Jan. 18, 2000 for "Motor Sensor System" (hereafter the "Herron Patent");
18. U.S. Pat. No. 6,917,865 issued to Arai et al. on Jul. 12, 2005 for "Engine Oil, Degradation-Determining System And Method, And Engine Control Unit" (hereafter the "Arai Patent");
19. United States Patent Application Publication No.: 2006/0114007 issued to Cho on Jun. 1, 2006 for "Apparatus, A method, And Measuring Sensors For Scanning States Of Engine Oil" (hereafter the "Cho Patent"); and
20. China Patent Application Publication No.: 03140986.5 issued to Sun on Dec. 3, 2003 for "Methods For Detecting Deterioration In Oil" (hereafter the "Sun Publication").

The Gary Patent discloses an invention of a water-in-fuel sensor circuit and method. The invention includes a reference capacitor coupled in parallel with a variable capacitor which is immersed in a fuel of a fuel tank, wherein two capacitors are alternately charged and discharged by an oscillator. Water in the fuel will cause increase of the effective capacitance value of the variable capacitor which reduces the absolute magnitude of the current that is detected. The absolute magnitude of the detected current can be utilized to indicate excessive water levels in the fuel.

The Yasuhara Patent illustrates an oil deterioration sensor and method. The oil deterioration sensor is comprised of a voltage divider which is constructed by a sensor capacitor and a fixed capacitor, wherein a constant frequency AC voltage source is applied to the voltage divider. Therefore a developed voltage across the sensor capacitor corresponds to the dielectric constant of the lubrication oil, from which the oil deterioration can be detected. The frequency of the AC voltage ranges from 50 KHz to 500 KHz.

The Kauffman Patent discloses a method for evaluating the remaining useful life of a hydrocarbon oil containing at least one additive species. A voltammetric analysis is applied to test the remaining amount of the additive, which results in amount of the redox current corresponding to the remaining amount of the additive species. Therefore, the remaining useful life can be concluded in accordance with the magnitude of the current.

The Park First Patent discloses an oil deterioration sensor. The sensor includes an oil deterioration sensor capacitor which is constructed with two metal plates, and a total reference capacitor which includes an external fixed reference capacitor. The respective capacitances of the oil deterioration capacitor and the total reference capacitor provide an engine oil deterioration indication for the oil deposited within a gap of the metal plates. The oil deterioration sensor further includes a temperature sensitive resistor thermally connected to a substrate of the sensor for providing a temperature adjustment to the engine oil deterioration indication, and a circuitry utilizing the capacitance of the respective oil deterioration sensor capacitor and the total reference capacitor to generate the engine oil deterioration indication.

The Park Second Patent discloses a combination of a capacitive oil deterioration and oil level sensor. The sensor comprises a conductive cylindrical housing member that includes a conductive shielding member defining a ground electrode, and a conductive inner member defining a measuring electrode. The sensor also includes electronics adapted to generate signals indicative to the deterioration of the oil deposited within a gap of two electrodes and a level of the oil along the length of the cylindrically shaped sensor. The oil level is monitored from detecting a ratio of the capacitance of oil dielectric constant over the capacitance of the oil level as $C_\in/C_L$.

The Park third patent discloses a sensor which has a similar main structure as the sensor of the Park Second Patent. In addition, the patented sensor applies electronics including at least one isolating capacitor to eliminate a flow of current between two electrodes that may cause a build up of material on the two electrodes that define the capacitor. This build up of unwanted material may cause an undesirable effect in the sensor output signal. The Park Third Patent further discloses the capacitance $C_\in$ of the oil deterioration and level sensor capacitor is proportional to $\in$ times L, where $\in$ is the dielectric constant of the oil and L is the length of the inner electrode. Therefor, the oil level affects the length of the inner electrode, which also affects the capacitance of the sensor.

The Gomm Patent discloses a portable oil change analyzer for a laboratory oil test, which is comprised of a viscosity analyzer and a contamination analyzer. The contamination analyzer is based on an optical mechanism, where increase of contaminates in oil results in decrease of a light intensity for an incident light after passing through the oil sample. The oil quality is determined by results from both viscosity and contamination tests.

The Meitzler Patent discloses an oil deterioration sensing system comprising an identical reference capacitor and sampling capacitor immersed in the respective fresh oil and sample oil under test. The system tests change of responded frequencies of the tested oil when both capacitors are under excitation of applied frequencies. Results of the test indicates change of the responded frequencies is consistent with change of the viscosity of the oil which is related to the aging of the oil.

The Marszalek Patent discloses a method for detecting quality of lubricating oil, which includes a sensor having two electrodes. The method includes applying a potential of a first amplitude to the electrodes immersed in an oil in use, testing a first voltage phase lag, increasing amplitude of the potential to a second amplitude, testing a second voltage phase lag. Therefor, the patented invention can determine the quality of the oil based on the voltage phase lags.

The Wang First Patent discloses a method of detecting engine oil if it is contaminated by presence of antifreeze. The method includes applying a series of different voltages to a sensor immersed in an oil in use, testing a corresponded series of the current sensor output voltages, determining a voltage difference between each of the current sensor output voltage relative to a reference voltage. Thereby determining if presenting the antifreeze in the oil after comparing the voltage differences.

The Wang Second Patent discloses a device for testing oil condition including an oil condition sensor having electrodes. The electrodes are separated by a gap that is filled with an engine oil. A processor connected to the sensor can be used to determine if the oil is at a first, second and third stage of oil degradation, which is corresponding to a first, second and third sensor output signal trend.

The Lvovich Patent discloses an apparatus and a method for monitoring a highly electrically resistive fluid. The method includes applying an AC signal that comprises at least two different AC electrical potentials, with at least one AC potential having a none-zero DC offset, measuring the fluid's electrical response including impedance and its real and imaginary components, thereby determining the fluid quality.

The Chopra Patent discloses an invention of electronic oil level and replacement system. The invention is based on the physical phenomenon that a position of a float member is dependent upon an level of the oil. Therefore, a change of the vertical position of the float member will cause a motion of a piston which opens or stops a passage to an oil reservoir. Therefore, the replacement system can work. Following the same mechanism, another float member can activate a lower oil level electric switch or an upper oil level electric switch according to the respective oil level, so that the oil level can be electrically detected.

The Halalay Patent illustrates a method to detect a change of oil resistivity over a period of elapsed times for an oil in use, which is consistent with to a change of the oil viscosity over the time. Therefore, the method can be applied to monitor oil deterioration including a remaining useful life of the oil.

The Schoess Patent discloses an apparatus for determining condition of the engine lubricating oil. The apparatus includes a sensor have a plurality of spaced apart electrode pairs on a nonconductive polymer film. A forcing-function waveform reactive circuit is applied to the sensor input electrode as a common voltage potential. The output current of the sensor output electrode is converted to an equivalent voltage. Based on the voltage values, the sensing apparatus will determine the oil's condition, and will therefore trigger a trouble code if the equivalent voltage falls within a predetermined range.

The Bauer Patent discloses a fluid condition monitor, comprising a capacitive spaced array electrode probe which is immersed in the fluid and is applied by an oscillating voltage. A first frequency of at least one hertz is applied and a corresponded first current of the electrode probe is measured. A second frequency is then applied and a corresponded second current is measured. Therefore a difference between the first and second current can be obtained, which can be used to predicated the fluid condition, as compared with a predetermined threshold value.

The Herron Patent discloses a motor sensor system for detecting the presence of water in a sealed oil chamber of an engine. The sensor system includes a plurality of flat conductive and insulative annular rings which are alternatively sandwiched together to be an assembly. The assembly is mounted on the propeller shaft in the sealed oil chamber of an engine. Each conductive ring is connected to a remote alarm circuit. In addition, the ring includes a plurality of radially inwardly extending probe sections which are circumferentially spaced around the propeller shift. Thus, if water enters the engine in running, a mixture of the oil and water spans one or more of the gaps formed between the complementary probe sections of the conductive element. Therefore, it completes the alarm circuit and provides an operator of the engine a warning of the water in the oil of the engine.

The Arai Patent discloses an engine oil degradation-determining system. The system applies a crankshaft angle sensor which detects the engine rotation speed of an internal combustion engine. Therefore, an electronic device calculates a cumulative revolution number indicative of a degradation degree of the engine oil. An oil level sensor detects an oil level of the engine oil, which is comprised of an upper limit switch and a lower limit switch. Basically, the upper switch monitors the oil level when it reaches a predetermined upper limit, and the lower limit switch monitors the oil level when it reaches a predetermined lower limit. Following this detection mechanism, the invention of the oil level sensor enables to monitor the oil level.

The Cho Patent Application Publication relates to an apparatus, a method, and measuring sensors for scanning engine oil of a vehicle. The invention includes a viscosity sensor which predominantly monitors the oil deterioration, and an oil level sensor which monitor the oil level. The oil level sensor in FIG. 8 has an input electrode 106 having a shape of pipe and installed to have an electric current applied thereto, and an oil level electrode 105 having a shape of a pipe installed apart from the inner surface of the input electrode 106 so as to receive the electric current from the input electrode 106. Therefore, the oil level is calculated on the basis of the capacitance and dielectric constant measured between the oil level electrode 105 and the input electrode 106.

The Sun Patent Application Publication discloses methods for detecting deterioration in oil, comprising a preferred embodiment having a reference and a sensing capacitor. Therefore, variations of electrical properties of the sensing capacitor, which are caused by the temperature variations, can be compensated by the same variations of electrical properties of the reference capacitor. This results in a temperature compensated electrical property of the sensing capacitor, which represents the oil deterioration. Following the same procedure a predicted temperature compensated electrical property profile for the used oil can be established including the property of the respective new oil and spent oil. The profile corresponds to a usage interval having usage of the respective new and spent oil. Therefore, a remaining usage ratio R can be calculated according to the obtained temperature compensated electrical property of the used oil, thereby to determine the remaining usage of the used oil as R times the usage interval. In addition, various methods are disclosed to detect presence of water in oil.

There is a significant need to have methods for detecting oil conditions including a top level of an oil system which is reduced to a top level of a threshold amount of the oil, and oil deterioration which occurs in the absence or presence of water, to significantly improve usage of the oil and protect machines which use the oil.

SUMMARY OF THE INVENTION

The present invention methods are directed to detect oil conditions including oil deterioration, oil level and a remaining usage of an oil. These conditions are critic for maintaining, thus protecting a machine which uses the oil, such as internal combustion engines and electrical transformers. The oil deterioration can be occasioned by factors such as the thermo-oxidative breakdown, additive depletion, water contamination, breakdown product polymerization, and carbon particulates which are produced in the combustion process. During its deterioration, the oil in use is usually consumed so that a top level of the oil is reduced. The methods of the present invention employ a sensing capacitor which is immersed in the oil and positioned to alien with a predetermined level of a threshold amount of the oil. Therefore, the oil deterioration or top level of the predetermined threshold amount of the oil can be determined from measuring one of various electrical properties of the capacitor.

In a situation during the oil deterioration when the amount of the oil is not significantly reduced so that the capacitor is still fully immersed in the oil, the electrical property of the capacitor is influenced by increase of the dielectric constant of the oil due to progress of the oil deterioration, or by significant increase of the dielectric constant due to presence of water in the oil. In another situation when the amount of the oil is significantly reduced to the predetermined threshold amount, it causes to lower a top level of the oil, which is insufficient for the sensing capacitor being fully immersed in the oil, so that the capacitor is partially filled with the air. According to this condition, the electrical property of the capacitor is predominantly influenced by the dielectric constant of the air which is substantially smaller than the dielectric constant of the oil.

In accordance with a first preferred embodiment of the present invention methods, a reference capacitor is also used in addition to the sensing capacitor. The reference capacitor is immersed in a reference oil including a dry new oil or a dry spent oil or a dry partially spent oil having the same thermal properties as those of the oil in use. The reference oil and the oil in use are placed in the same temperature environment. In addition, the reference capacitor has defined structural parameters so that the sensing and reference capacitors exhibit the same change of the electrical property according to the oil temperature change when they are immersed into the same oil. In the first preferred embodiment, the electrical properties of the sensing and reference capacitors are combined, thereby eliminating fluctuations of the measured electrical property of the sensing capacitor, where the fluctuations are induced by variations of the oil temperature. Therefore, from a first measurement the preferred embodiment of the present invention enables to obtain a first measured temperature compensated electrical property of the sensing capacitor, which represents a first measured temperature compensated electrical property of the oil that is known not to contain water. In this manner, a predicted temperature compensated electrical property profile for the oil also can be simulated, which correlates a full range of actual usages of the oil to thereby represent an entire deterioration for the oil when it is dry. Within the profile, it can determine a first predicted temperature compensated electrical property $EP_T(P)$ of the oil as compared with the first measured temperature compensated electrical property, wherein they are correlated to a same first actual usage of the oil.

Applying the measured temperature compensated electrical property, a measured remaining usage of the oil can be obtained from the present invention, so as to a predicted remaining usage for the oil according to the predicted temperature compensated electrical property. Following the first measurement, the present invention applies a second measurement according to the same first actual usage of the oil, which obtains a second measured temperature compensated electrical property so as to a second measured remaining usage of the oil. Comparing the first predicted remaining usage for the oil with the second measured remaining usage, a normal oil deterioration, the oil deterioration which occurs in the absence of the water contamination between two measurements, can be concluded if the second measured remaining usage of the oil is similar to the first predicted remaining usage. Therefore, the second measured remaining usage of the oil can be confirmed as the actual remaining usage, which is useful for a user of the machine to set a schedule of the oil change.

If the second measured remaining usage of the oil is apparently shorter than the first predicted remaining usage, an abnormal oil deterioration, the oil deterioration which occurs in the presence of the water contamination, can be concluded. This conclusion is based on a fact that the dielectric constant of water is substantially larger than the oil dielectric constant, which causes that the measured temperature compensated electrical property of the sensing capacitor filled with the mixture of the oil and water is different from the predicted electrical property of the same capacitor fully filled with the oil. The difference further leads to a false phenomenon of the shortened measured remaining usage for the oil mixed with water.

If the second measured remaining usage of the oil is noticeably longer than the first predicted remaining usage, it can conclude that a top level of the oil is reduced to the top level of a predetermined threshold amount of the oil. In this situation, the sensing capacitor which is positioned to align with the top level of the predetermined threshold amount of the oil is partially filled with air. Since the dielectric constant of the air is substantially smaller than the oil dielectric constant, the measured property of the capacitor partially filled with the air is different from the predicted property of the same capacitor fully filled with the oil. The difference further leads to a false phenomenon of the prolonged measured remaining usage of the oil.

Obtaining the above illustrated abnormal oil conditions, the user of the machine can take appropriate actions to protect the machine from damage.

Besides of applying the second remaining usage of the oil, the first preferred embodiment of the present invention also can conclude that water is likely to be present in the oil in application of the second measured temperature compensated electrical property.

From comparing the second measured temperature compensated electrical property of the oil with the first predicted temperature compensated electrical property, the first preferred embodiment of the present invention further can conclude that the top level of the oil is reduced to a top level of the threshold amount of the oil if the second measured temperature compensated electrical property differs from the first predicted temperature compensated electrical property, where the difference indicates less deterioration of the oil than deterioration determined by the first predicted temperature compensated electrical property.

The present invention also discloses variations of the first preferred embodiment, which comprise at least two sensing capacitors. The at least two sensing capacitors can be placed to different locations of an oil system of the machine so that the user of the machine can determine if there is an uneven distribution of the oil deterioration through the entire oil system. This information is particularly useful for a large size internal combustion engine such as one equipped to a locomotive or ship, where water can exist in particular locations of the oil system. If the at least two sensing capacitors can be positioned along a vertical orientation, a change of a full range of the oil level can be monitored when the oil amount is gradually consumed so as to gradually lower the top oil level. Accordingly, each of the at least two sensing capacitors will change sequentially from a capacitor filled with the oil to one filled with air. Therefore, an in situ oil top level can be monitored from detecting such sequential change of the electrical properties of the respective at least two sensing capacitors.

In accordance with a second preferred embodiment, the present invention only applies the sensing capacitor. A measured temperature compensated electrical property profile of the capacitor can be obtained so as to a predicted property profile, according to a number of known temperature compensation methods. Under this situation, the second embodiment further enables to derive the second measured remaining usage of the oil. Therefore, the second embodiment of the present invention can determine oil conditions including a top oil level which is reduced to a top level of the predetermined threshold amount of the oil during the oil reduction process, the abnormal oil deterioration and normal oil deterioration including a confirmed actual remaining usage of the oil, following the same strategy of comparing the second measured remaining usage with the first predicted one. In addition, the second embodiment further enables to apply at least two sensing capacitors for monitoring if there is an uneven distribution of the oil deterioration or a change of a full range of the oil level in the machine.

It is therefore an object of the present invention to obtain a measured temperature compensated electrical property of a sensing capacitor from applying a reference capacitor, so that variations of the electrical property of the sensing capacitor, which are induced by the temperature variations, can be compensated by the same variations of the property of the reference capacitor.

It is also an object of the present invention to quantitatively describe deterioration of an oil in use from establishing a predicted temperature compensated electrical property profile with applying a dry new oil or a dry partially spent oil or a dry spent oil having respective known usages, so that an oil under measurement can be determined for its deterioration, from comparing a second measured temperature compensated electrical property of the oil with a first predicted temperature compensated electrical property from the predicted property profile.

It is also a further object of the present invention to quantitatively describe a remaining usage of an oil from establishing a measured remaining usage ratio as $R_M=[EP_T(M)-EP_{T,S}]/[EP_{T,N}-EP_{T,S}]$, which leads to a measured remaining usage as $R_M$ $\Delta U_F=R_M\times(U_S-U_N)$, and a corresponding predicted remaining usage ratio and remaining usage in a similar fashion, if there is a linear relationship between the temperature compensated electrical properties of the oil and the respective usages of the oil.

It is also another object of the present invention to quantitatively describe a remaining usage of an oil from establishing a measured actual remaining usage as $\Delta U_M=(U_S-U_M)$, and a corresponding predicted actual remaining usage in a similar fashion, if there is non linear relationship between the temperature compensated electrical properties of the oil and the respective usages of the oil.

It is a further object of the present invention to compare if the second measured remaining usage is respective shorter than, similar to and longer than the first predicted remaining usage, so that the present invention can conclude the oil conditions including the respective abnormal oil deterioration, normal oil deterioration, and a top oil level which is reduced to the top level of a predetermined threshold amount of the oil.

It is an additional object of the present invention to apply at least two measurement sensors which are positioned at the respective different locations through an entire oil system, so that the present invention enables to determine if there is an uneven distribution of deterioration of the oil including if water is accumulated to the respective locations in the oil system.

It is a further additional object of the present invention to apply at least two measurement sensors including first and second of the respective at least two measurement sensors which are positioned at the respective different levels of the oil system, wherein the first of the at least two measurement sensors is positioned whose sensing capacitor is aligned with a level that is adjacent and below a top level of the oil which is newly replaced, and the second of the at least two measurement sensor is positioned whose sensing capacitor is aligned with the top level of a threshold amount of the oil, so that a detailed information can be obtained for reduction of the top level of the oil in the oil system.

Other features and advantages of the present invention will become apparent from the following detailed description, taken in conjunction with the accompanying drawings, which illustrate, by way of example, the principles of the invention.

BRIEF DESCRIPTION OF THE DRAWINGS

Referring particularly to the drawings for the purpose of illustration only and not limitation, there is illustrated

FIG. 5 is a circuit diagram showing an impedance measurement using a voltage divider;

FIG. 6 is a circuit diagram showing a current measurement using a constant voltage source;

FIG. 7 is a circuit diagram showing a voltage measurement using a constant current source;

FIG. 8 is a graph showing profiles of the respective impedance (Z), voltage (V), and current (I) for an oil which deteriorates over the time;

In FIG. 16 the independent variable is presented as the time "t";

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Oil conditions are critic for maintaining, thus protecting a machine which uses an oil. The conditions include abnormal deterioration of the oil which occurs in the presence of water, or normal deterioration of the oil which occurs in the absence of water and contains a remaining usage of the oil that is useful for a schedule to change the oil, and a top level of the oil in the machine when it is reduced to a top level of a threshold amount of the oil. The present invention methods are aimed to detect these conditions from applying a single measurement sensor, thereby providing respective indications to a user of the machine for taking appropriate actions to protect the machine from damage. The methods are disclosed in the following two sections.

I. Methods for Detecting Deterioration of an Oil

In a machine such as an internal combustion engine, lubricating oil is used to reduce friction between moving engine parts. Over time however the oil deteriorates and is therefore less effective in protecting the engine from damage. The life span of the oil is limited by factors such as the thermo-oxidative breakdown, additive depletion, water contamination, breakdown product polymerization, and carbon particulates which are produced in combustion of the engine operation.

Figure 1:
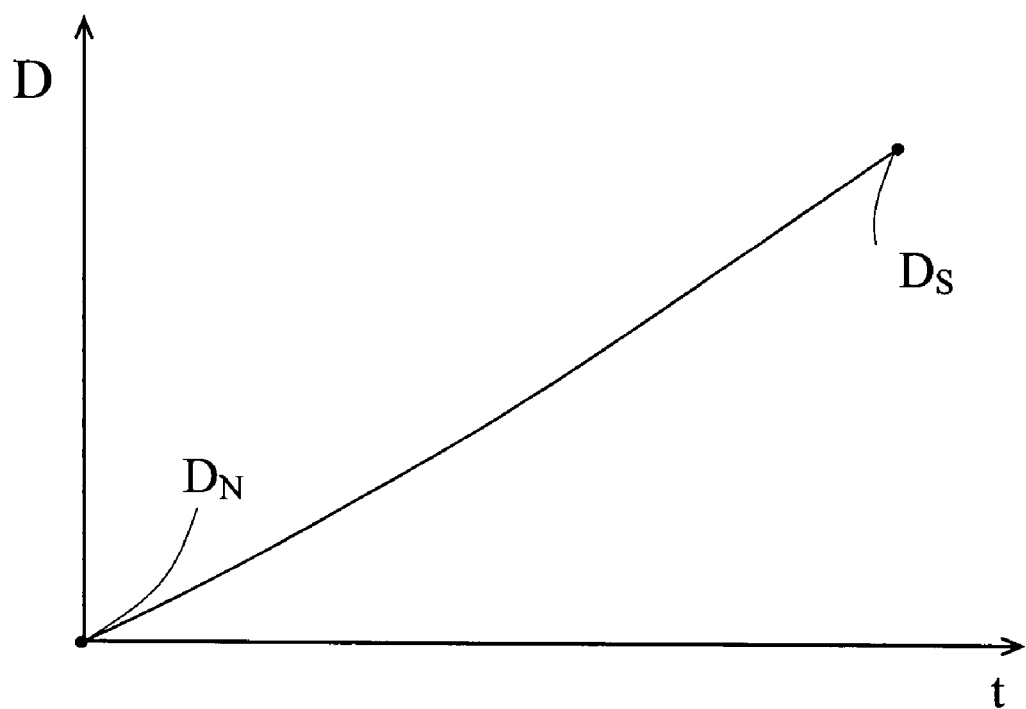
FIG. 1 is a graph showing deterioration of an oil in use as the function of time.

Within the above mentioned facts, the water contamination effects differently, as compared with the rest of facts to effect the oil chemical, physical and electrical properties. Therefore, it will be appreciated that oil deterioration can be classified as the normal one which occurs in the absence of water and the abnormal one which occurs in the presence of water. FIG. 1 shows a normal oil deterioration profile (D) according to the elapsed times (t). When an oil is new or unused there is no deterioration, which is shown at a point "$D_N$". As time progresses and the oil is used, contaminants build up. Eventually, the deterioration reaches a point "$D_S$" when the oil is spent and should be changed.

Similarly, the oil used in power transformers is subject to breakdown. Primary causes for deterioration include heat, oxygen, moisture, and electrical stress: partial discharge and arching.

It is well known that the dielectric constant of the oil increases with increase of the oil contamination and thus deterioration. Therefore, by making use of this property, a degree of the oil deterioration may be measured electrically. This can be done by placing a sensor such as a capacitive probe (C) in the oil and measuring the electrical properties of the oil as manifested by electrical properties of the probe. As contaminants build up the deterioration progressively occurs and the dielectric constant ($\in$) of the oil increases leading to an increase of the probe's capacitance ($C_p$).

Figure 2:
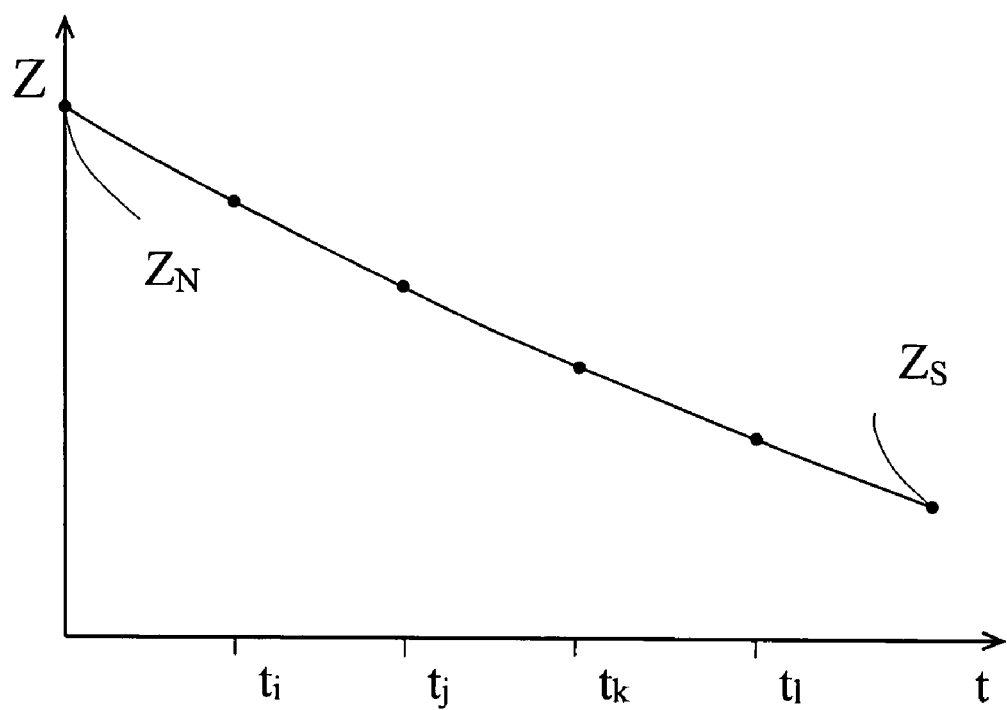
FIG. 2 is a graph showing decrease of impedance of the oil as the function of increase of the elapsed times according to the oil deterioration illustrated in FIG. 1.

The increase of the capacitance causes a decrease of the impedance (Z) of the oil according to the equation $Z=R+j(-1/\omega C)$. The decrease of the impedance in turn increases the current (I) which flows between the plates of the capacitive probe when an AC voltage (V) is applied across the plates. Such technology is well known in the art, and is specifically disclosed in U.S. Pat. No. 4,646,070. FIG. 2 illustrates during the normal oil deterioration a decrease of the impedance (Z) as a function of an increase of the used times of the oil. The impedance value "$Z_N$" is high for the new or unused oil, and the impedance value "$Z_S$" is low for the spent oil. Additionally, since oil is basically non-conductive, the capacitive reactance $j(-1\omega C)$ or ($X_c$), a component of the impedance is the predominant factor to govern the value of the impedance. Referring to FIG. 2, it will be appreciated that a user may periodically measure the impedance to determine the quality of the oil (denoted by dots). Measurement may range anywhere from continuous to infrequent.

Figure 3:
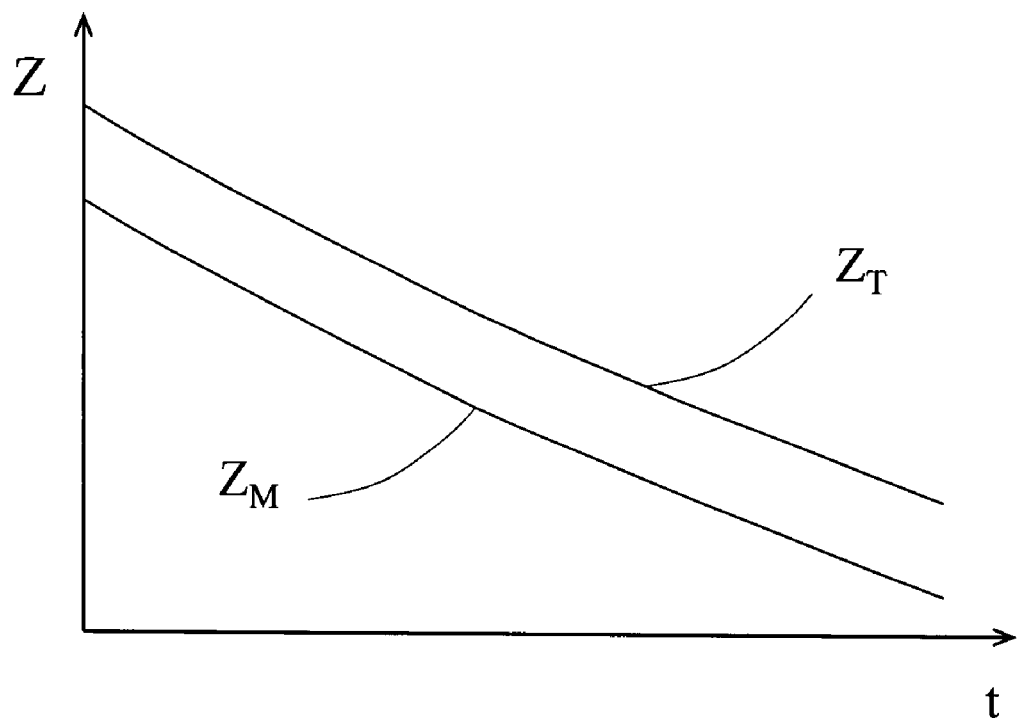
FIG. 3 is a graph showing relationship between a profile of measured impedance $Z_M$ and a profile of temperature compensated impedance $Z_T$.

However, it is noted that values of the dielectric constant of the oil are also influenced by the temperature variations, which cause variations of the capacitance of the capacitor so as to the impedance. Therefore, it is necessary to eliminate this temperature effect in the measurement by "compensating" variations of the measured impedance. This may be done by measuring a temperature of the oil and applying a correction factor to convert a value of the measured impedance ($Z_M$) to a value of the actual or temperature compensated impedance ($Z_T$). Also, a temperature compensated measurement can be made by always measuring the oil at a predetermined temperature. FIG. 3 shows relationship between a profile of the measured impedance ($Z_M$) and a profile of the temperature compensated impedance ($Z_T$) according to the used times, wherein the time is an independent variable that is expressed as a particular type of the oil usage.

Figure 4:
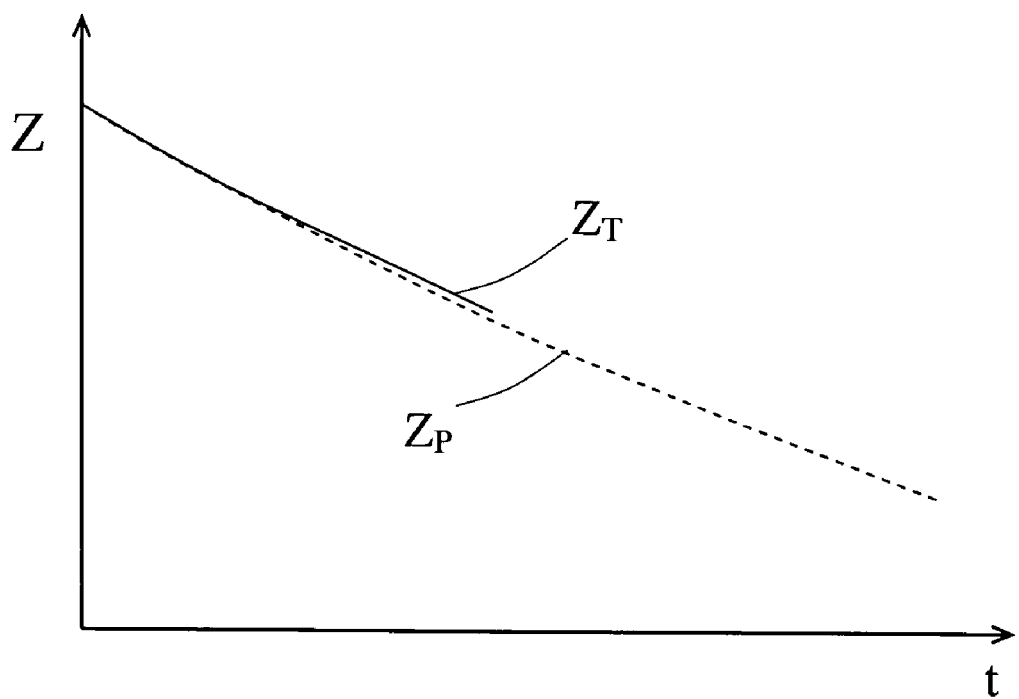
FIG. 4 is a graph showing a profile of predicted temperature compensated impedance $Z_P$, which is consistent with a profile of actual temperature compensated impedance $Z_T$.

FIG. 4 is a graph showing a profile of the predicted temperature compensated impedance ($Z_P$) as compared with a profile of the actual or measured temperature compensated impedance ($Z_T$). The profile of the predicted impedance ($Z_P$) is anticipated, which decays smoothly as the function of the times. This indicates the normal deterioration of the oil. The predicted curve of impedance ($Z_P$) could be developed empirically through test measurements. In the illustrated example, the actual impedance ($Z_T$) closely follows the predicted impedance ($Z_P$). This is a further indication of the normal oil deterioration. However, as it will be discussed later, certain influences can cause the predicted values to differ from the respective actual values of the impedance.

Referring to FIGS. 2-4, the oil deterioration has been shown in terms of the impedance measurement. Such impedance measurement may be made by placing a sensing capacitor in series with a known impedance to form a voltage divider, and applying an AC voltage across the impedance of the capacitor and the known impedance. The ratio of a voltage across the capacitor to a voltage across the known impedance is proportional to the impedance of the capacitor, which is the representation of the oil impedance.

It will be appreciated however, that the oil deterioration could also be represented and measured in terms of a current (I) flowing through the capacitor as a result of an applied constant voltage, or in terms of a voltage (V) developed across the capacitor as a result of an applied constant current. Any of these measurements may be performed using techniques well known in the electrical art. As in the case of the measured current and voltage they must also be temperature compensated.

Methods of measuring the various electrical properties of the capacitor are shown in FIGS. 5-7. The capacitor (C) can be constructed with two or more metal conductors in parallel having a spaced gap between two adjacent conductors for sufficient oil circulation. FIG. 5 is a circuit diagram which illustrates the impedance measurement using a voltage divider. An alternating voltage source ($V_A$) applies a potential across a capacitor (C) connected to a reference impedance ($Z_{ref}$) of known value. The impedance of the capacitor (C) represents the deterioration of the oil. In one embodiment, the reference impedance ($Z_{ref}$) is a resistor.

FIG. 6 is a circuit diagram for the current measurement using a constant voltage source ($V_0$). The current (I) through the capacitor (C) represents the deterioration of the oil.

FIG. 7 is a circuit diagram for the voltage measurement which uses a constant current source $I_0$. The voltage (V) across the capacitor C represents the deterioration of the oil.

FIG. 8 is a graph which illustrates profiles of the respective impedance, voltage, and current of the capacitor filled with an oil which deteriorates according to the elapsed times. It is of course noted that the impedance and voltage will decrease smoothly as the oil deterioration in progress, and that the current will correspondingly increase as development of the oil deterioration.

It will be appreciated that the impedance could be further separated into its imaginary component: capacitive reactance ($X_c$), which is equal to $j(-1/\omega C)$, and real component: resistance (R). Therefore, either of these measured components of the impedance, using procedures well known in the art, can provide an indication of the oil deterioration. Such measurements can be made using an impedance analyzer such as an Agilent 4294A to obtain impedance, reactance, resistance, capacitance, and phase angle. It is noted that phase angle can be determined by resistance and reactance.

Figure 10:
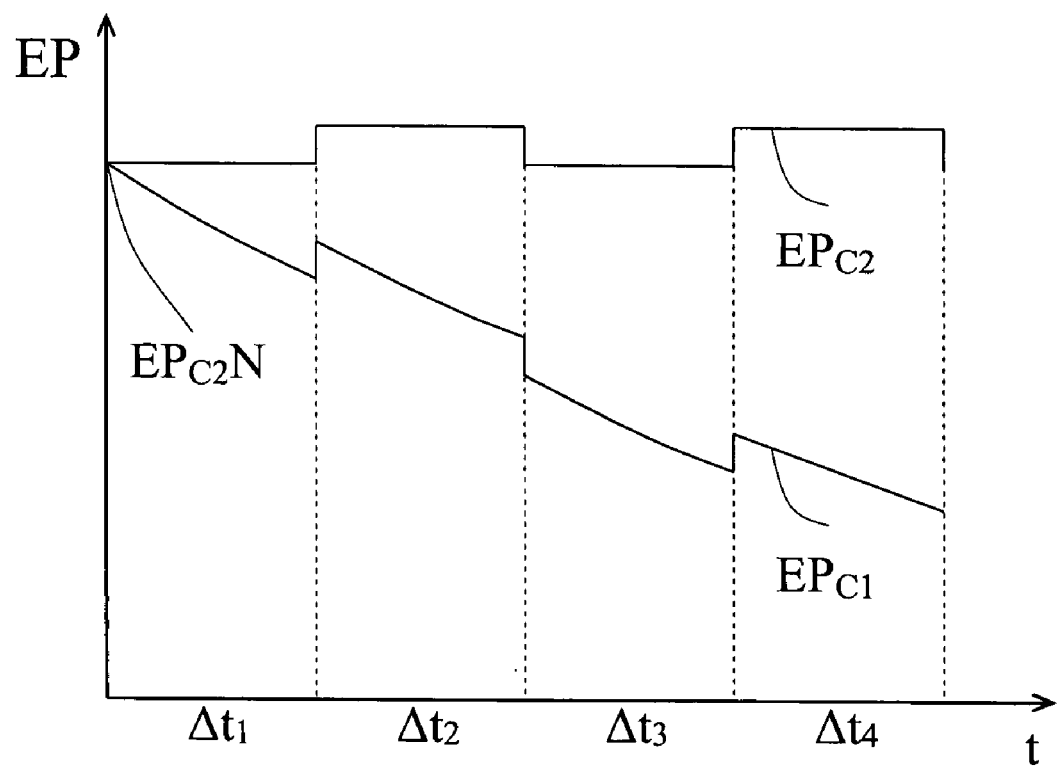
FIG. 10 is a graph which shows electrical property profiles of the respective sensing capacitor and reference capacitor without the temperature compensation.

Now referring to FIGS. 9-11, 13 and 14, there is illustrated a method in accordance with a first preferred embodiment of the present invention for detecting oil conditions including a top level of the predetermined threshold amount of the oil, or an abnormal deterioration of the oil which occurs in the presence of water, or a normal deterioration of the oil which occurs in the absence of water and contains a remaining usage of the oil. In this embodiment, a reference sensor is utilized to compensate variations of the measured electrical properties, which are induced by the temperature variations. The method includes:

(a) providing an oil 22 in use which does not contain water and is disposed in an oil system including an oil reservoir of a machine such as a crankcase 34 of an engine or a container of an electrical transformer;

(b) providing a reference oil 24 disposed in a sealed container which is located in a common temperature environment with the oil 22. The reference oil 24 is free of water;

In the preferred embodiment, the reference oil 24 has the same thermal properties as the oil 22. That is, temperature variations cause the electrical properties of the reference oil 24 and the electrical properties of the oil 22 to change in a like manner. Also in the preferred embodiment, the reference oil can be either (1) an unused oil, or (2) a spent oil, or (3) a partially spent oil. For example, the reference oil 24 which is illustrated in FIG. 10 is the unused oil of the same brand and type as the oil 22.

(c) providing a measurement sensor 26 which includes a first capacitor (C1) as a sensing capacitor;

In the preferred embodiment, the measurement sensor 26 may further include a container which has a plurality of openings for allowing oil circulation in addition to protect the sensing capacitor placed inside of the container. Therefore the container of the sensor is represented to be the dashed lines in FIG. 9.

(d) providing a reference sensor 28 which includes a second capacitor (C2) as a reference capacitor. The reference sensor 28 includes the sealed container wherein the reference capacitor (C2) is fully immersed in the reference oil 24.

In a preferred embodiment on their related structural parameters, the first and second capacitors should both exhibit the same change in the electrical properties according to the oil temperature change when they are immersed into the same oil. Also, it will be appreciated that the measurement sensor 26 and reference sensor 28 can be arranged into an integrated mechanical unit.

(e) positioning the measurement sensor 26 to the oil system wherein the sensing capacitor (C1) is fully immersed in the oil 22;

(f) using a measuring device for measuring an electrical property $EP_{C1}$ of the first capacitor (C1) and electrical property $EP_{C2}$ of the second capacitor (C2) from a first measurement, wherein the electrical property is one of:

the impedance of the first capacitor and impedance of the second capacitor;

the current passing through the first capacitor and current passing through the second capacitor;

the voltage developed across the first capacitor and voltage developed across the second capacitor;

(g) combining the electrical property $EP_{C1}$ of the first capacitor with the electrical property $EP_{C2}$ of the second capacitor to obtain a first measured temperature compensated electrical property of the sensing capacitor, which represents a first measured temperature compensated electrical property $EP_{T,i}(M)$ of the oil. This oil property may represent deterioration of the oil 22; Here the symbol "$EP_{T,i}(M)$" is used to represent the property of the oil, where the subscribed letter "T" indicates the temperature compensation, "i" indicates a first measurement at a first usage "i" and the letter "M" means the electrical property "EP" which is obtained through measurement.

Figure 9:
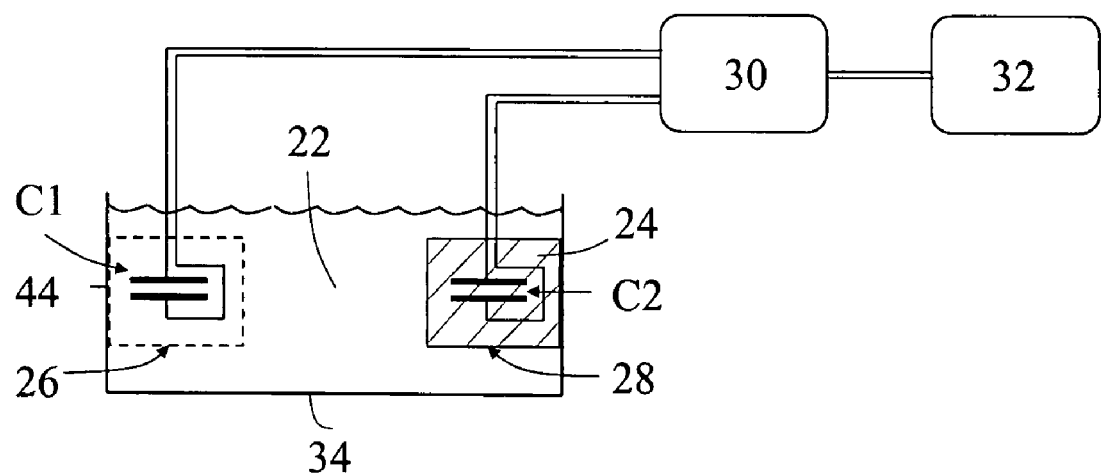
FIG. 9 is a diagram of an apparatus from a first preferred embodiment of the present invention where a temperature compensated electrical property is developed.

Referring to FIG. 9, the electrical property ($EP_{C1}$) of the first capacitor and the electrical property ($EP_{C2}$) of the second capacitor are combined in a measurement device 30 to result in the first measured temperature compensated electrical property of the sensing capacitor, which can be routed to a display 32 for presentation to the user under the user's choice.

Figure 11:
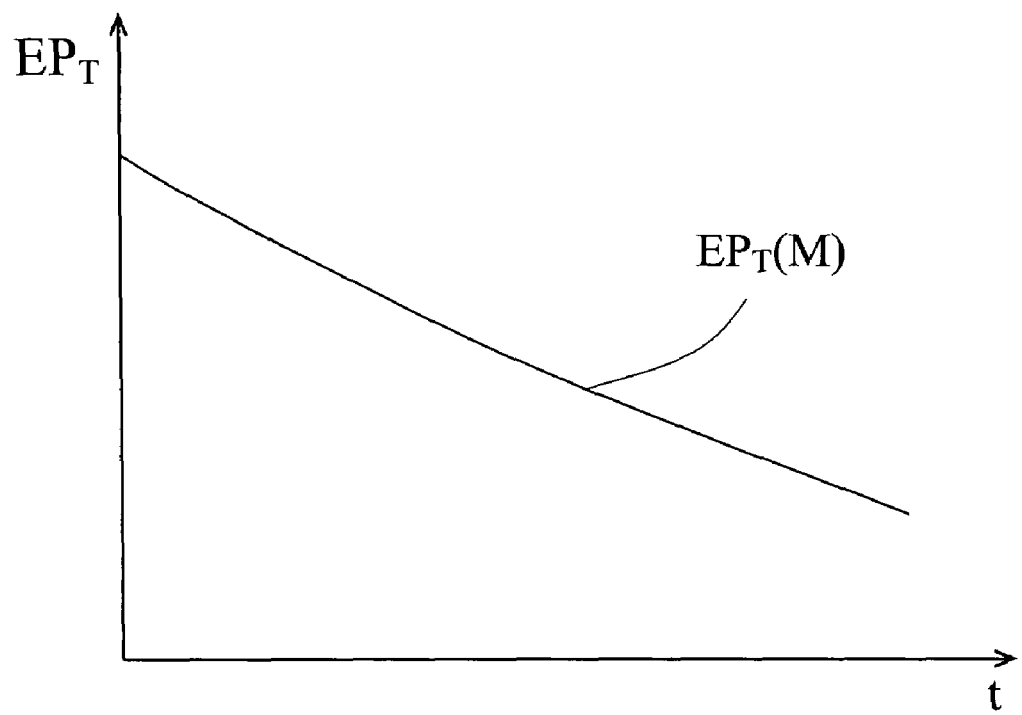
FIG. 11 is a graph which shows a profile of measured temperature compensated electrical properties $EP_T(M)$ of the sensing capacitor as derived from FIG. 10.

Referring now to FIGS. 10 and 11, there is illustrated how the variations of the electrical property ($EP_{C1}$) can be compensated by applying the reference capacitor (C2) from the present invention. In this embodiment, the reference oil is the unused oil or the new oil of the same brand and type as the oil 22. As illustrated, during the time interval ($\Delta t_1$), the electrical property ($EP_{C2}$) of the second or reference capacitor has a constant value ($EP_{C2}N$). However, during the time period ($\Delta t_2$) the value ($EP_{C2}$) increases due to a change of the oil temperature. Similarly, during the time interval ($\Delta t_3$) the value returns to the normal one, and during the time period ($\Delta t_4$) the value again increases due to a temperature change. In addition, it will be appreciated that the reference oil is sealed separately, so that it is not subject to conditions caused by operation of the machine, and thus it does not deteriorate during the entire life of its usage. This is illustrated by its vale ($EP_{C2}N$) that is unchanged over the times, wherein ($EP_{C2}N$) is a normal value of the electrical property of the second capacitor filled with the new oil.

Such behavior of the electrical property ($EP_{C2}$) is utilized as a baseline to correct or compensate the electrical property ($EP_{C1}$) of the first or sensing capacitor filled with the oil, which is also influenced by the temperature variations. In addition, the electrical property of the first capacitor is also influenced by the progress of the oil deterioration according to the oil usage of the elapsed times. Therefore, the oil is changed starting from a new oil when the oil is unused to a spent oil when the oil is completely used. For this reason, the initial property of the first capacitor is the same as ($EP_{C2}N$) of the second capacitor.

It will be appreciated that the temperature change effects the electrical property ($EP_{C1}$) and electrical property ($EP_{C2}$) in an identical fashion since both capacitors are in the same temperature environment, the respective filled oils have the same or similar thermal properties, and the capacitors are constructed by the defined structural parameters. Therefore, by combining electrical property ($EP_{C1}$) and electrical property ($EP_{C2}$) according to a below-cited equation [1], the result is a measured temperature compensated electrical property $EP_T(M)$ of the sensing capacitor, which may be the representation of the oil deterioration.

It will be appreciated that the shown curve for the electrical property in FIG. 11 is one for the impedance or voltage. If the measured property is the current, the curve would be as that shown in FIG. 8.

Referring to FIG. 11, there is illustrated that the measured electrical properties of the respective capacitors (C1) and (C2) have been combined to result in a measured temperature compensated electrical property $EP_T(M)$ at each measurement over the entire life of usages of the oil starting from the new oil which deteriorates to be the spent oil, thereby to form a profile of the measured temperature compensated electrical properties $EP_T(M)$. In a preferred embodiment of combining the electrical properties of the respective two capacitors, variations of the electrical property ($EP_{C1}$) of the sensing capacitor (C1) due to the temperature variations are essentially subtracted from the same variations of the electrical property ($EP_{C2}$) of the reference capacitor (C2) in accordance with the following equation [1]:

$$EP_T(M) = EP_{C1} - EP_{C2} + EP_{C2}N \quad [1]$$

From the equation, the value ($EP_{C2}N$) can be a value including the nominally measured value of $EP_{C2}$, which positions $EP_T(M)$ along the positive values of the y axis in FIG. 11. Referring to the figure, the y axis represents the temperature compensated electrical properties ($EP_T$) of an oil including the new, partially spent and spent oil. The x axis is each of the elapsed times during deterioration of the oil.

However, it will be another appreciated that other methods of combining ($EP_{C1}$) and ($EP_{C2}$) such as ($EP_{C1}-EP_{C2}$) could also be employed so long as the electrical property ($EP_{C2}$) of the second or the reference capacitor (C2) is utilized to remove the temperature effects from the electrical property ($EP_{C1}$) of the first or the sensing capacitor (C1). Further, if combining the properties through ($EP_{C2}-EP_{C1}$), a deterioration profile of the oil can be obtained, which is similar to the one in FIG. 1.

Also, referring to FIGS. 9-11, and as previously mentioned in step (f) above, the electrical property could be one of the components of the impedance, resistance (R) or capacitive reactance ($X_c$), rather than the total composite impedance. Measurement procedures and equipments well known in the art could be used to make such measurements, for this or other oil measurement methods disclosed herein.

It will be appreciated that as described herein the "unused" oil is a new or fresh oil which is essentially free of contaminants. The "partially spent" oil is an oil that has been in use for some period of time, and therefore has some build up of contaminants. Also, the profile of the measured temperature compensated electrical properties $EP_T(M)$ shown in FIG. 11 utilizes the time as the independent variable. However, other parameters besides the time could also be utilized. For example in a motor vehicle a profile of the temperature compensated electrical properties ($EP_T$) could be expressed as the function of a usage of the oil, such as traveled miles rather than the used times.

Figure 12:
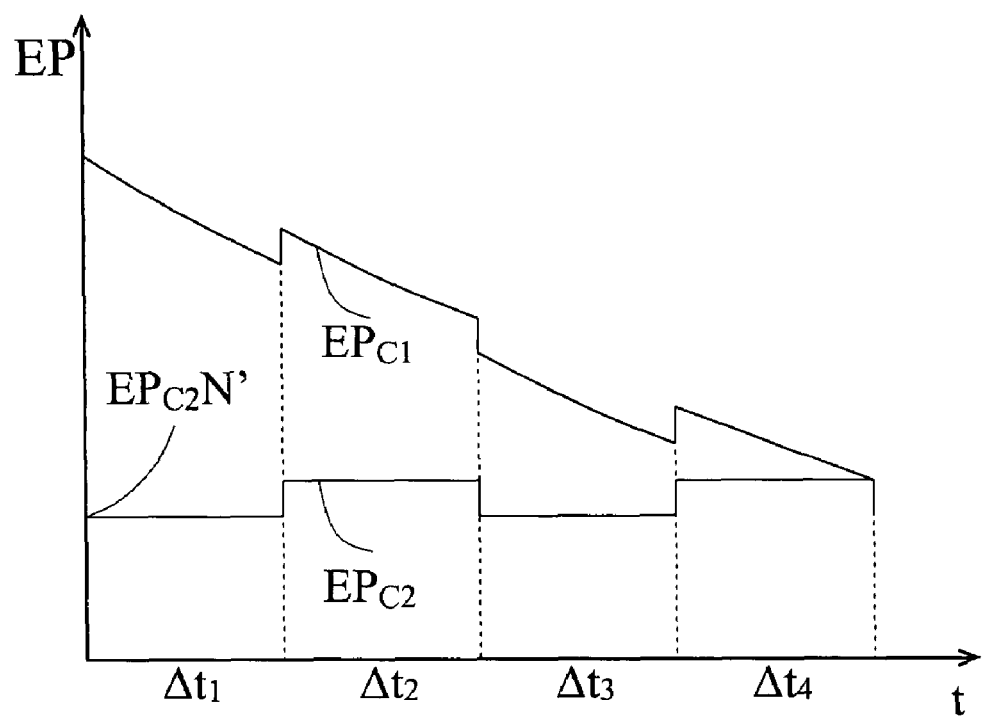
FIG. 12 is a second graph to illustrate electrical property profiles of the respective sensing capacitor and reference capacitor without temperature compensation.

FIG. 12 illustrates an alternative method for compensation of the temperature effects. In this embodiment the spent oil rather than the unused oil is used as the reference oil. Therefore, the sensing capacitor (C1) is immersed in the oil 22 as before, but the reference capacitor (C2) is immersed in the reference oil 24 which is the spent oil having its normal value ($EP_{C2}N'$). The spent oil is an oil with large concentrations of contaminants, and therefore whose lubricating properties are effectively exhausted. The spent oil used as the reference oil 24 preferably has the same thermal properties as the oil 22. In the respective time periods ($\Delta t_2$) and ($\Delta t_4$) a same change in oil temperature causes the same increase in both electrical properties ($EP_{C1}$) and ($EP_{C2}$).

It will be appreciated that if the measured electrical properties of the respective capacitors (C1) and (C2) in FIG. 12 have been combined as before, a resulted profile of the measured temperature compensated electrical properties $EP_T(M)$ of the oil is identical to the profile shown in FIG. 11. It will be further appreciated that through the later discussions, the above disclosed measured properties $EP_T(M)$ can serve as the representation of the oil deterioration or oil level according to the respective situations.

In addition, following the above disclosed steps (a) to (g), it can obtain a profile of the predicted temperature compensated electrical properties $EP_T(P)$ for the oil 22, wherein the letter "P" means the electrical properties "EP" which are predicted according to the respective known usages. The profile represents progress of the normal deterioration for the oil in its entire life of usages if the oil is dry. The profile includes a temperature compensated electrical property ($EP_{T,N}$) for a new oil when the oil is new or unused, and a temperature compensated electrical property ($EP_{T,S}$) for a spent oil when the oil is spent. Between the temperature compensated electrical properties ($EP_{T,N}$) and ($EP_{T,S}$), there are various different temperature compensated electrical properties ($EP_{T,PS}$) for the respective partially spent oils. The temperature compensated electrical properties ($EP_{T,PS}$) represent the oil when it is dry at different stages of the oil deterioration according to the respective usages of the oil.

It will be appreciated that for illustration of the present invention, the definition of "a profile of measured temperature compensated electrical properties $EP_T(M)$" is identical to the respective definitions "a measured temperature compensated electrical property profile", "a measured property profile", and "a profile of the measured properties $EP_T(M)$". Similarly, the definition of "a profile of predicted temperature compensated electrical properties $EP_T(P)$" is identical to the respective definitions "a predicted temperature compensated electrical property profile", "a predicted property profile", and "a profile of the predicted properties $EP_T(P)$". In addition, the "measured temperature compensated electrical property (properties) $EP_T(M)$" and "predicted temperature compensated electrical property (properties) $EP_T(P)$" can be simply addressed as the respective "measured property (properties) $EP_T(M)$" and "predicted property (properties) $EP_T(P)$". Similarly, the "temperature compensated electrical property $EP_{T,N}$", "temperature compensated electrical property $EP_{T,S}$" and "temperature compensated electrical property $EP_T$" can be simply addressed as the respective "property $EP_{T,N}$", "property $EP_{T,S}$" and "property $EP_T$".

The profile of the predicted properties $EP_T(P)$ for the oil can be obtained from various previously disclosed methods. Hereafter is an example for experimentally simulating the entire deterioration for the oil 22 when it is dry to obtain the profile of the predicted properties $EP_T(P)$. When the oil is new or unused which obviously does not contain water, the new oil is tested following the above disclosed steps (a) to (g), which results in the property ($EP_{T,N}$). Then the dry new oil is experimentally used for a purpose to make it deteriorated according to a predetermined period of the experimental times. It will be appreciated that experimental conditions are the same as or mostly close to conditions of the real usage of the oil. The dry new oil then becomes a partially spent dry oil to have a predetermined degree of deterioration which correlates to the experimental times. Then the dry oil having the known degree of deterioration is measured following the above disclosed steps (a) to (g), which results in a ($EP_{T,PS}$) that is a predicted property $EP_T(P)$ according to the known degree of the oil deterioration. The dry oil having the known degree of deterioration is experimentally used for the second time according to the same predetermined period of the experiment times, where all the experimental conditions are kept the same for the entire experiment of oil deterioration. Thus it causes the dry oil further partially deteriorated. Then the further partially deteriorated oil is measured again following the above disclosed steps (a) to (g), which results in a temperature compensated electrical property that represents a larger degree of the oil deterioration, as compared with the prior property ($EP_{T,PS}$). Following this manner to complete the oil deterioration, the oil is deteriorated to the spent oil. Therefore, the profile of the predicted temperature compensated electrical properties $EP_T(P)$ can be established, which represents the normal oil deterioration that occurs for the oil 22 if it is dry. It will be appreciated that the reference oil also can be applied for obtaining such profile of the predicted properties $EP_T(P)$ since the reference oil is a dry oil having the same brand and type as the oil 22, which is disclosed before.

Therefore, the first embodiment of the present invention continually comprises the following step:

(h) following the steps (a) to (g) establishing a predicted temperature compensated electrical property profile for the oil, which represents the normal oil deterioration, the predicted property profile includes a property ($EP_{T,N}$), which is equal to a measured property $EP_T(M)$ of the oil if it is unused or new and dry, and another electrical property ($EP_{T,S}$), which is equal to a measured property $EP_T(M)$ of the oil if it is spent and dry.

Figure 13:
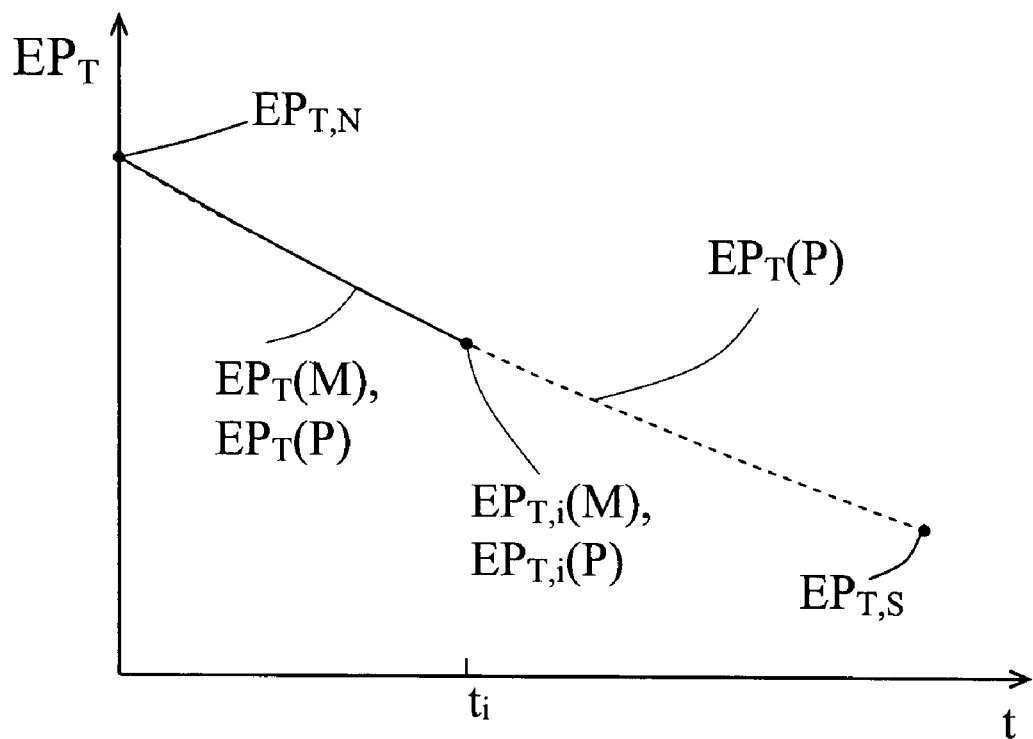
FIG. 13 is a graph showing a profiles of the respective measured and predicted temperature compensated electrical properties during a normal deterioration of the oil, where the profiles are presented in accordance with the independent variable of the elapsed times.
Figure 14:
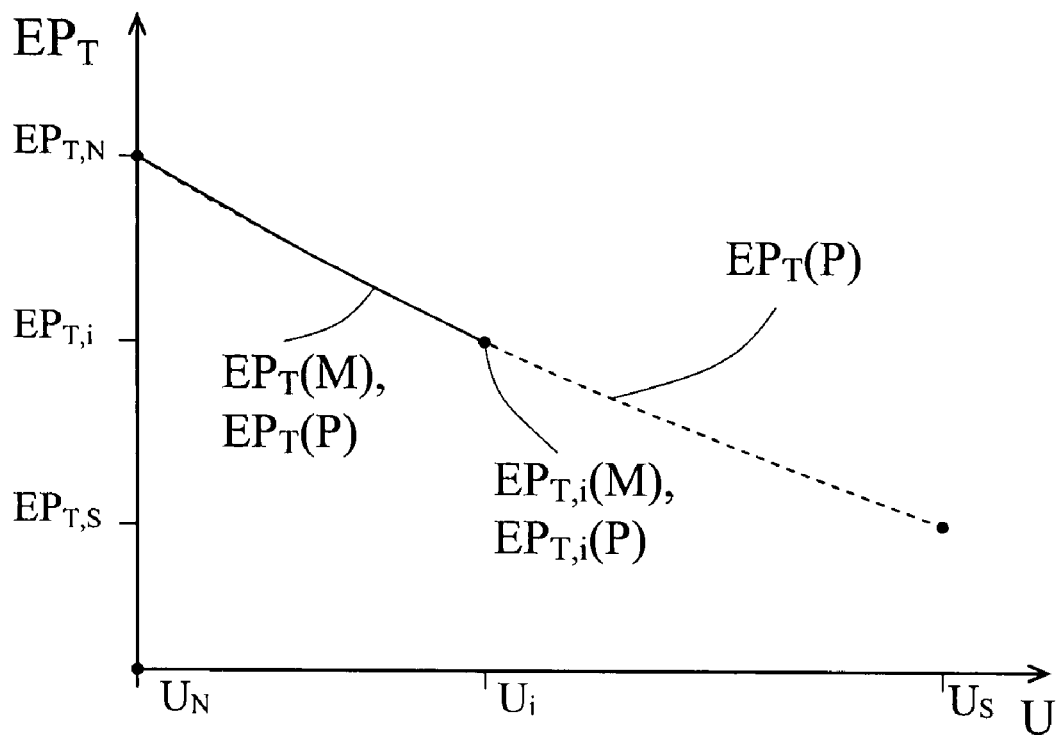
FIG. 14 is a graph showing the same profiles of the respective measured and predicted temperature compensated electrical properties during the normal deterioration of the oil in FIG. 13. However, the profiles are presented according to the independent variable of usage of the oil which includes the used times or the traveled miles.

Now the normal oil deterioration, which has been briefly disclosed in FIG. 4, will be illustrated in detail in FIGS. 13 and 14. FIGS. 13 and 14 illustrate the same situation of the normal oil deterioration, where a partial profile of the measured properties $EP_T(M)$ is consistent with a corresponding section of the profile of the predicted properties $EP_T(P)$. It will be appreciated that, for a comparison with an abnormal oil deterioration in later discussion, the partial of the measured property profile is presented in the respective figures.

Referring to FIG. 13, the predicted property profile includes the properties of the respective new oil, spent oil and partially spent oils, which is presented as the dashed line. The partial of the measured property profile, which is presented as the solid line, includes the properties of the respective new oil and oil in use. The partial profile of the measured properties $EP_T(M)$ illustrates that the new oil has been used thus deteriorated in a period of times that ends at a point of time ($t_i$), which corresponds to a measured property $EP_{T,i}(M)$. The measured property $EP_{T,i}(M)$ is a first measured property $EP_T(M)$ from a first measurement which serves an example to illustrate how the present invention applies measured and predicted properties to determine conditions of the oil. Accordingly, the predicted property profile of the oil also contains a predicted property $EP_{T,i}(P)$ according to the point of time ($t_i$) which serves as a first predicted property $EP_T(P)$ of the example of the present invention. As illustrated, the first measured property $EP_{T,i}(M)$ has the same value, as compared with that of the first predicted property $EP_{T,i}(P)$.

Now referring to FIG. 14, it illustrates the same measured and predicted property profiles as disclosed in FIG. 13. However, instead of using the time as the independent variable, FIG. 14 employs an actual usage of the oil (U) as the variable, which can also be simply addressed as "usage" in the following disclosure. Therefore, the properties ($EP_{T,N}$) and ($EP_{T,S}$) of the respective new and spent oil are related to the respective usages ($U_N$) and ($U_S$). The usage ($U_S$) represents a number of the traveled miles or used times of the spent oil during the entire life of usages of the oil which is changed from the new oil to the spent oil. It will be appreciated that due to the consistency between the predicted and measured properties, the electrical properties of the respective new and spent oil are presented as the respective same properties ($EP_{T,N}$) and ($EP_{T,S}$) regarding their respective measured and predicted properties $EP_T(M)$ and $EP_T(P)$. Accordingly, a full range of usages of the oil $\Delta U_F = (U_S - U_N)$ is defined relative to the electrical property change ($EP_{T,N} - EP_{T,S}$). In addition, FIG. 14 further illustrates that the first measured property $EP_{T,i}(M)$ is consistent with the first predicted property $EP_{T,i}(P)$ related to the same first usage ($U_i$), which represents the normal deterioration of the oil.

Obtaining the above mentioned information, the first embodiment of the present invention continually comprises the following steps:

(i) establishing a full range of actual usages for the oil as $(\Delta U_F) = (U_S - U_N)$ according to change of the properties as ($EP_{T,N} - EP_{T,S}$), wherein a symbol (U) represents an actual usage of the oil which is an independent variable to the property ($EP_T$), so that the ($U_N$) is an actual usage of the oil which is new or unused and the ($U_S$) is an actual usage of the oil which is spent;

(j) defining a first measured normalized remaining usage ratio ($R_{M,i}$) of the oil having the first measured property $EP_{T,i}(M)$ which correlates to a first actual usage of the oil as:

$$R_{M,i} = [EP_{T,i}(M) - EP_{T,S}]/[EP_{T,N} - EP_{T,S}],$$

wherein the ($R_{M,i}$) ranges from one for the oil that is new or unused and dry to zero for the oil that is spent and dry, which can be simply addressed as "a first measured ratio ($R_{M,i}$)".

And further defining a first measured remaining usage of the oil as $R_{M,i} \Delta U_F = R_{M,i} \times (U_S - U_N)$ from the first measurement.

Accordingly, a first measured normalized deterioration ratio ($D_{M,i}$) of the oil having the first measured property $EP_{T,i}(M)$ can be defined as:

$$D_{M,i} = [EP_{T,N} - EP_{T,i}(M)]/[EP_{T,N} - EP_{T,S}]$$

ranging from zero for the new oil to one for the spent oil, which can be simply addressed as "a first measured ratio ($D_{M,i}$)".

In addition, it can be similarly established for a first predicated normalized remaining usage ratio ($R_{P,i}$), which can be simply addressed as "a first predicted ratio ($R_{P,i}$)" according to a first predicted property $EP_{T,i}(P)$ from the predicted property profile. For example, there is the first predicted property $EP_{T,i}(P)$ in the respective FIGS. 13 and 14 according to the respective first time ($t_i$) and usage ($U_i$). The first predicated ratio $R_{P,i}$ is equal to $[EP_{T,i}(P) - EP_{T,S}]/[EP_{T,N} - EP_{T,S}]$, which leads to a first predicted remaining usage ($R_{P,i} \Delta U_F$), and a first predicated normalized deterioration ratio $D_{P,i} = [EP_{T,N} - EP_{T,i}(P)]/[EP_{T,N} - EP_{T,S}]$ that can be simply addressed as "a first predicted ratio ($D_{P,i}$)".

According to the illustration of FIG. 14, it will be appreciated that the first measured ratio ($R_{M,i}$) is consistent with the first predicted ratio ($R_{P,i}$) according to the same first usage ($U_i$). Therefore the first measured remaining usage ($R_{M,i} \Delta U_F$) is also consistent with the first predicted remaining usage ($R_{P,i} \Delta U_F$). In this situation, it concludes the normal deterioration of the oil, plus the first measured remaining usage which is confirmed as the actual remaining usage of the oil.

Therefore, continuing from the previous step (j) of the method, the present invention has the following step:

(k) from the predicted property profile, determining a first predicted property $EP_{T,i}(P)$ according to the same first actual usage $U_i$ as compared with the first measured property $EP_{T,i}(M)$, from which establishing a first predicated normalized remaining usage ratio as $R_{P,i} = [EP_{T,i}(P) - EP_{T,S}]/[EP_{T,N} - EP_{T,S}]$ and a first predicted remaining usage ($R_{P,i} \Delta U_F$) of the oil;

It also can conclude that determining a normal deterioration of the oil which occurs in the absence of water if the first measured remaining usage ($R_{M,i} \Delta U_F$) is similar to the first predicated remaining usage ($R_{P,i} \Delta U_F$), and confirming the first measured remaining usage which represents an actual remaining usage of the oil;

It will be appreciated that similarity between the measured and predicted remaining usages can always be easily and quantitatively defined by a predefined threshold value in application of the present invention.

It will be further appreciated that the above mentioned first measured or first predicted ratio ($R_{M,i}$) or ($R_{P,i}$) which has been derived according to an approximation of the linear relationship between the change of the properties as ($EP_{T,N} - EP_{T,S}$) and the range of usages as ($U_S - U_N$). Therefore, the first measured remaining usage ($R_{M,i} \Delta U_F$) is a close approximated value to a first actual remaining usage.

It will be additionally appreciated that a normalized first measured remaining usage ratio (R') also could be mathematically derived, which is based on a possible nonlinear relationship between the change of the properties as ($EP_{T,N}-EP_{T,S}$) and range of usages as ($U_S-U_N$).

However, despite shapes of the respective predicted and measured property profiles a measured actual remaining usage is always correctly presented as: $\Delta U_M=(U_S-U_M)=(U_S-U_i)$. Referring to FIG. 14, ($U_i$) is the usage ($U_M$) of the oil at the traveled miles "i" or spent times "i", which correlates to the both first measured and predicted properties $EP_{T,i}(M)$ and $EP_{P,i}(P)$ during the normal oil deterioration. Therefore, a first predicted actual remaining usage is $\Delta U_P=(U_S-U_P)$, which is equal to the first measured actual remaining usage $\Delta U_M=(U_S-U_M)$ since the respective first predicted and measured usages $U_P$ and $U_M$ are equal to the usage $U_i$. This also proves the normal deterioration of the oil, and confirms the measured actual remaining usage.

Now referring to FIG. 14 again, there is illustrated that up until the first usage ($U_i$), the predicted properties $EP_T(P)$ are consistent with the measured properties $EP_T(M)$. This indicates the oil in use which is deteriorating in a predicted manner. However, as will be subsequently discussed, events occurring at the first usage ($U_i$) cause a value of a measured property $EP_T(M)$ to differ from a value of a predicted property $EP_T(P)$.

Figure 15:
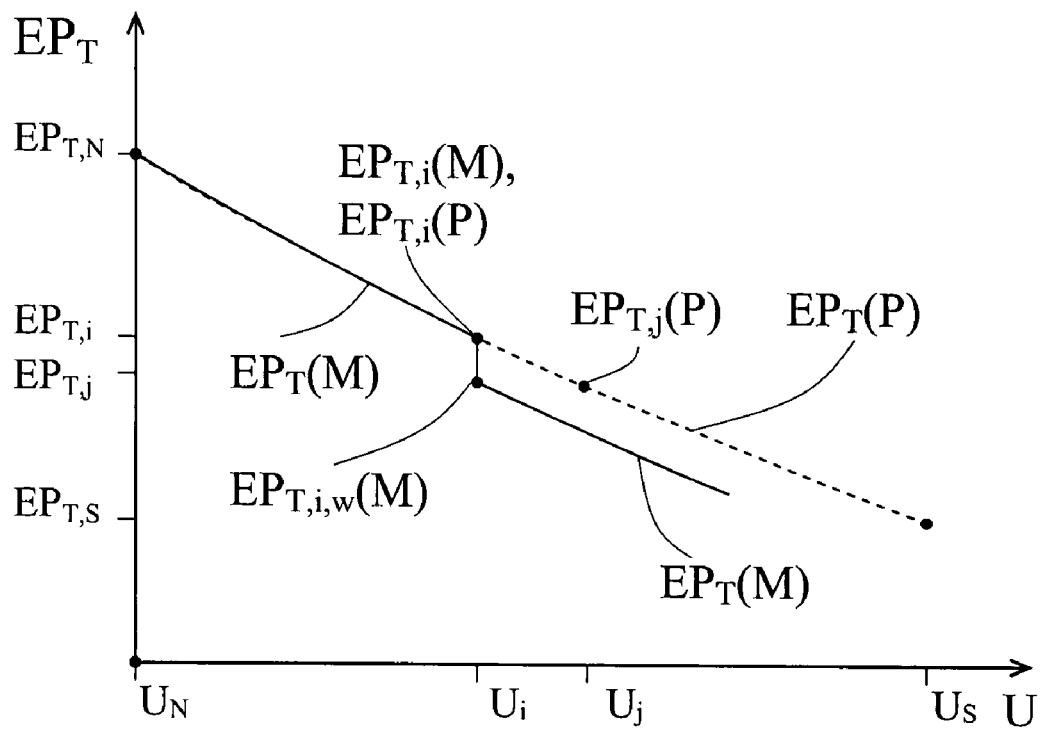
FIG. 15 is a graph showing the same curves in FIG. 14 including the predicted temperature compensated electrical property profile and a measured temperature compensated electrical property profile according to usages of the oil. The difference is that the measured property profile staring at an usage "$U_i$" has a sudden change, which illustrates extra deterioration of the oil than it should be.

Reference to FIG. 15 illustrates detection of an abnormal deterioration of the oil which occurs in the presence of water, wherein it is at the first usage ($U_i$) that the presence of water happens. As illustrated in FIG. 15, there is a sudden change of the first measured property $EP_{T,i}(M)$ from the first measurement to a second measured property $EP_{T,i,w}(M)$ from a second measurement, as compared with the first predicted property $EP_{T,i}(P)$ which represents the normal oil deterioration that occurs in the absence of water. In addition, since the first usage ($U_i$), the measured property profile consistently departs from the predicted property profile.

Figure 16:
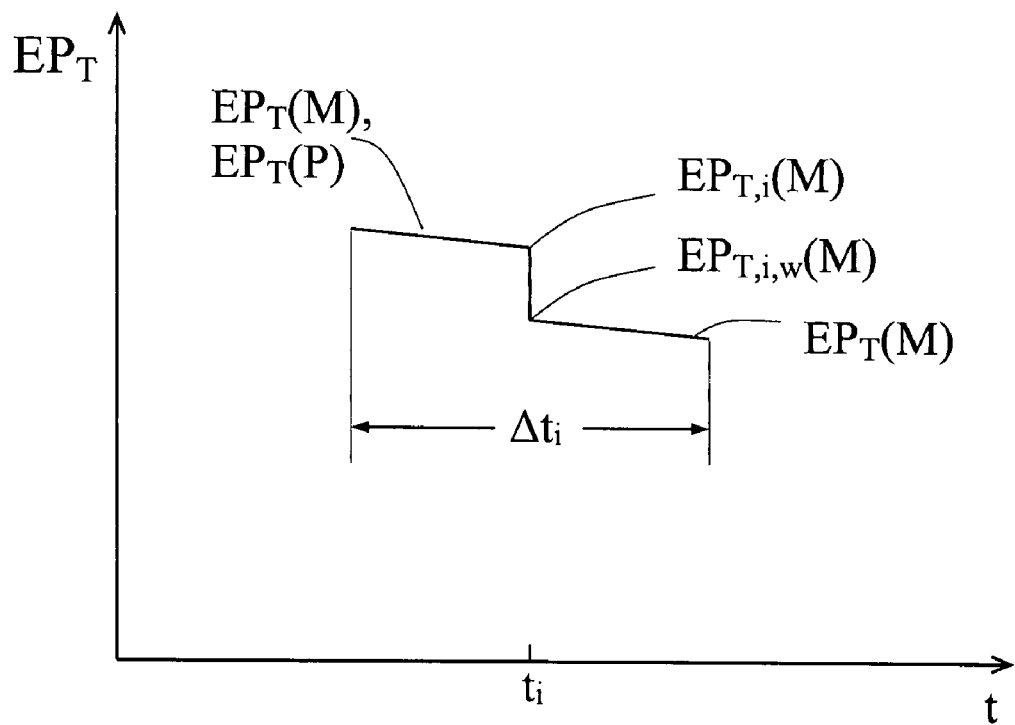
FIG. 16 is a graph which magnifies a section of the measured property profile in FIG. 15 wherein the profile has the sudden change at the usage "$U_i$".

For a detailed illustration, FIG. 16 magnifies a section of the measured property profile according to the first usage ($U_i$) when the sudden change of the measured properties occurs. However, the time is used as the independent variable in FIG. 16. In this embodiment, the likely presence of water in the oil is detected. For example, in an internal combustion engine, a head gasket could be partially ruptured at a small scale. An initial presence of the small rupture allows water suddenly to enter into the oil system, which causes the corresponding sudden change of the measured property $EP_T(M)$. It will be appreciated that the electrical property of the sensing capacitor could possibly be effected by other factors, however the sudden change in electrical properties is likely to be the result of the water contamination. This is because that the dielectric constant of water is significantly larger (approximately 3-4 times) than the dielectric constant of an oil.

The presence of water in the oil will reduce the impedance of the sensing capacitor or the voltage developed across the capacitor, and correspondingly increase the current flowing through the capacitor filled with the mixture of water and oil. Therefore, the fact of suddenly presenting water in the oil will cause the sudden change of the electrical properties of the sensing capacitor, which is presented as extra deterioration of the oil, as compared with the normal deterioration that is determined by the predicted property $EP_T(P)$.

Referring to FIG. 16 again, there is illustrated that it is at the first moment ($t_i$) of the time interval ($\Delta t_i$), the first measured property $EP_{T,i}(M)$ of the impedance or voltage from the first measurement has a sudden drop to the second measured property $EP_{T,i,w}(M)$ from the second measurement, wherein the letter (w) denotes the presence of water. As further illustrated, during the rest of the time interval ($\Delta t_i$), the measured property profile continuously decreases to align with its initial slope or an initial pattern of changing the properties, which exists prior to the first moment ($t_i$). This is because of the continuous presence of a constant small amount of water due to a dynamic water balance in the oil such as when an extra amount of water could be evaporated.

As compared with FIG. 16 which describes the water presence during the small time interval ($\Delta t_i$), FIG. 15 particularly illustrates how the presence of water in the oil causes a change of the measured temperature compensated electrical property and the corresponding remaining usage as well, as compared with the respective predicted values.

Referring to FIG. 15 since the first usage ($U_i$), the oil mixed with the constant small amount of water exhibits a pattern of the measured properties $EP_T(M)$, which is the same as a pattern of the predicted properties $EP_T(P)$ for the oil without the constant small amount of water. Therefore, a value of the second measured property $EP_{T,i,w}(M)$ for the oil mixed with the constant small amount of water is equal to a value of a predicted property $EP_{T,j}(P)$ for the oil without the constant small amount of water according to the profile of the predicted properties $EP_T(P)$. Apparently, the value of the predicted property $EP_{T,j}(P)$ is less than that of the first predicted property $EP_{T,i}(P)$. This means that the oil which is mixed with the constant small amount of water acts as a dry oil which is spent more than it should be, or which has extra deterioration as compared with deterioration predicted by the first predicted property $EP_{T,i}(P)$. Therefore, a second measured normalized remaining usage ratio for the oil mixed with the constant small amount of water at the first usage ($U_i$) is equivalent to a predicted normalized remaining usage ratio ($R_{P,j}$) for the oil at usage ($U_j$), where $R_{P,j}=[EP_{T,j}(P)-EP_{T,S}]/[EP_{T,N}-EP_{T,S}]$. In addition, the ratio $R_{P,j}$ further determines a predicted remaining usage ($R_{P,j} \Delta U_F$) which is equivalent to the second measured remaining usage from the second measurement.

It will be appreciated that the predicted ratio $R_{P,j}$ is smaller than the first predicted ratio at the first usage ($U_i$), $R_{P,i}=[EP_{T,i}(P)-EP_{T,S}]/[EP_{T,N}-EP_{T,S}]$. This results in that the predicted remaining usage ($R_{P,j} \Delta U_F$) is also less than the first predicted remaining usage ($R_{P,i} \Delta U_F$). However, the first predicted remaining usage ($R_{P,i} \Delta U_F$) is predicted for the oil during the normal deterioration; of the oil in the absence of water. Therefore, it can conclude that an abnormal deterioration of the oil is due to the water presence, where the second measured remaining usage will be less than the first predicted remaining usage ($R_{P,i}\Delta U_F$) relative to the same first actual usage. It will be appreciated that the above disclosure is a general conclusion, which serves to predict presence of water in the oil for any situations, as long as the sensing capacitor which is fully immersed in the mixture of the water and oil.

Thus, the present invention continually has the following steps to conclude the normal and abnormal deterioration of the oil which occurs in the respective absence and presence of water after the prior step "k":

(l) repeating steps (f) and (g) from a second measurement to obtain a second measured temperature compensated electrical property of the first capacitor which represents a second measured temperature compensated electrical property of the oil according to the first actual usage, from which obtaining a second measured remaining usage ratio and second measured remaining usage;

(m) determining a normal deterioration of the oil which occurs in the absence of water if the second measured remaining usage is similar to the first predicated remaining usage ($R_{P,i}\Delta U_F$), and confirming the second measured remaining usage which represents an actual remaining usage of the oil;

(n) determining an abnormal deterioration of the oil which occurs in the presence of water if the second measured remaining usage is less than the first predicated remaining usage ($R_{P,i}\Delta U_F$).

It will be appreciated that the step (in) is based on the previous conclusion of a normal deterioration of the oil which occurs in the absence of water if the first measured remaining usage ($R_{M,i}\Delta U_F$) is similar to the first predicated remaining usage ($R_{P,i}\Delta U_F$). The step (m) is also reasonable since all of the measured remaining usages will be similar to the first predicted remaining usage ($R_{P,i}\Delta U_F$) for the oil being free of water if multiple times of measurement are conducted at the same first actual usage of the oil.

Besides the above disclosed method which compares the second measured remaining usage with the first predicted remaining usage to conclude the presence of water in the oil, there is an alternative way in use of an actual remaining usage, which can also reach the same conclusion. Referring to FIG. 15, there is illustrated that the second measured property $EP_{T,i,w}(M)$ at the first usage ($U_i$) due to the water presence is equal to the predicted property $EP_{T,j}(P)$ at an usage ($U_j$). Therefore, a second measured actual remaining usage for the oil mixed with the constant small amount of water is equal to $\Delta U_M = (U_S - U_M) = (U_S - U_j)$, wherein the usage $U_M$ is corresponding with the second measured property $EP_{T,i,w}(M)$ so that $U_M$ is equivalent to $U_j$. As a comparison, the first predicted property $EP_{T,i}(P)$ represents the normal oil deterioration at the usage ($U_i$) and a first predicted actual remaining usage for the oil without the constant small amount of water is equal to $\Delta U_P = (U_S - U_P) = (U_S - U_i)$. Apparently the value of the ($\Delta U_M$) is less than the value of the ($\Delta U_P$), which also leads to the same conclusion of the abnormal deterioration of the oil which occurs in the presence of water if the second measured actual remaining usage $\Delta U_M$ is less than the first predicated actual remaining usage $\Delta U_P$. In contrast, referring to FIG. 15 again it can be easily understood that a normal deterioration of the oil can be concluded from a consistency of the measured and predicted actual remaining usages $\Delta U_M$ and $\Delta U_P$ if it is either according to the first measurement or according to the second measurement at the first usage $U_i$. It will be appreciated that the above analysis is particularly appropriate to the situation having the non linear relationship between the properties and usages.

In addition, the present invention can detect a likely presence of water in the oil as below, which applies the second measured temperature compensated electrical property:

observing a likely presence of water in the oil 22 if the following occur:

the second measured temperature compensated electrical property exhibits a sudden change which indicates extra deterioration of the oil than deterioration predicted by the first predicted property $EP_{T,i}(P)$; and the second measured temperature compensated electrical property has a value which differs from the first predicted property $EP_{T,i}(P)$, wherein the difference indicates extra deterioration of the oil than deterioration predicted by the first predicted property.

Figure 17:
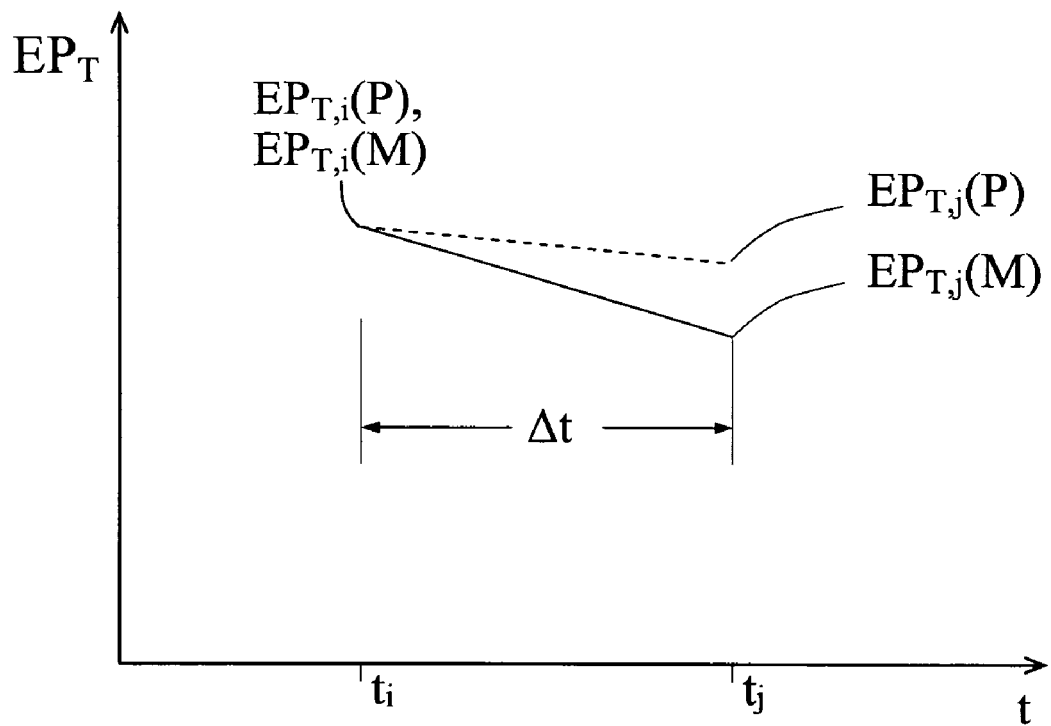
FIG. 17 is a graph which shows that a profile of measured temperature compensated electrical properties during the time period of $t_i$ and $t_j$ has a steeper slope than the slope of predicated property profile.

Now referring to FIG. 17, there is illustrated another embodiment of the present invention applying the property ($EP_T$) for detecting the abnormal oil deterioration which occurs in the presence of water. FIG. 17 illustrates an event happened during a period of the used times $\Delta t=(t_j-t_i)$ wherein $t_i$ is a first usage of time and $t_j$ is a second usage of time. The event causes inconsistency of the respective measured and predicted property profiles, including that a second measured property $EP_{T,j}(M)$ is smaller than a second predicted property $EP_{T,j}(P)$ relative to the same second usage of time ($t_j$). This contradicts that the respective first measured and predicted properties $EP_{T,i}(M)$ and $EP_{T,i}(P)$ have the same value at the first usage of time $t_i$. In this embodiment, the likely presence of water in the oil can be detected by comparing a rate of change of the measured properties $EP_T(M)$ with a rate of change of the predicted properties $EP_T(P)$, wherein the measured properties $EP_T(M)$ of the oil exhibit a faster rate towards the oil deterioration. Obviously, the rate is expressed as $\Delta EP_T/\Delta t$. Therefore, the faster rate from the measured properties indicates extra deterioration of the oil than the oil deterioration predicted by the predicted properties.

It will be appreciated that an increased water amount in the oil over the time is the most likely reason to cause the above illustrated phenomenon. This could be happened if the rupture of the head gasket is big enough, which allows a large amount of water to enter into the oil system so that the dynamic water balance in the oil cannot be maintained, as compared with the condition illustrated in FIG. 16.

Figure 18:
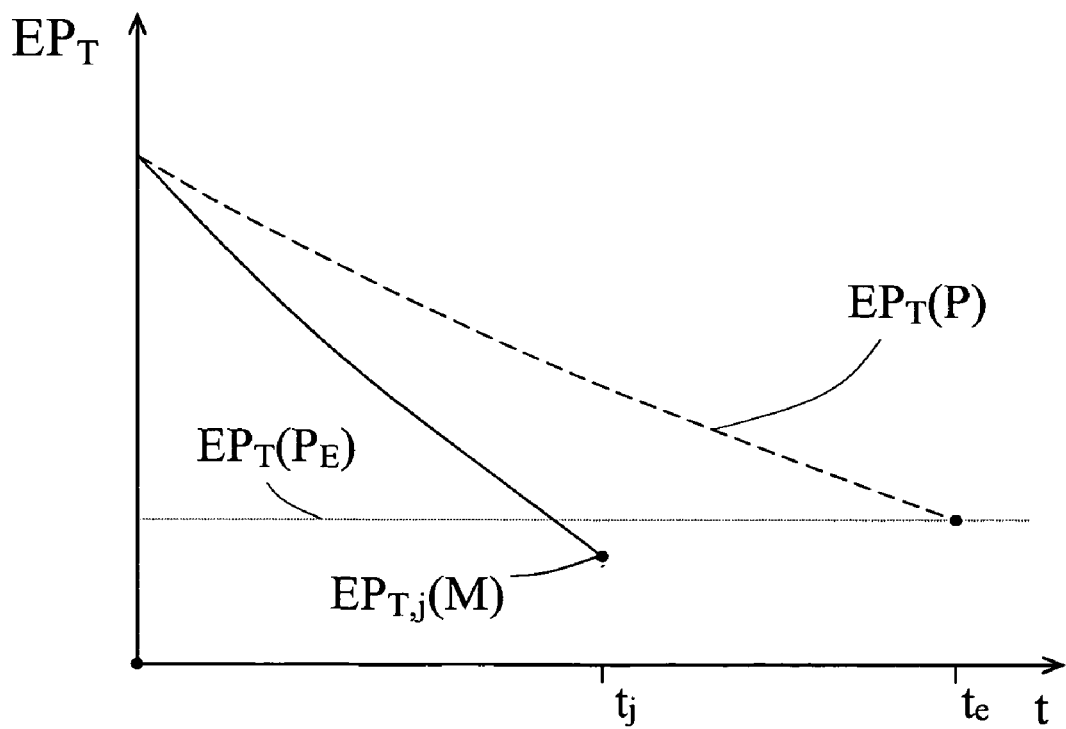
FIG. 18 is a graph showing a measured temperature compensated electrical property profile which exceeds a predetermined extreme value of the predicted temperature compensated electrical property before it should be.

In addition to situations which are illustrated in FIGS. 16 and 17, FIG. 18 illustrates an additional situation where water could be in the oil. Referring to FIG. 18, the measured and predicted property profiles have a common value at a very beginning. However, there is illustrated second measured property $EP_{T,j}(M)$ at a time ($t_j$), which exceeds a predetermined extreme value $EP_T(P_E)$ of the predicted property at a time ($t_e$) from a profile of the predicted properties $EP_T(P)$. In addition, the second measured property $EP_{T,j}(M)$ exceeds the predetermined extreme value at the time ($t_j$) which is earlier than the predicted time ($t_e$): ($t_j<t_e$). Of course earlier could be earlier in times, earlier in miles, etc. This too is an indication of presence of water in the oil.

Therefore, according to the illustrations of FIGS. 17 and 18 the methods for detecting the likely presence of water in the oil comprise the claims as bellow:

observing a likely presence of water in the oil 22 if any of the following occur:

the first and second measured temperature compensated electrical properties related to the respective first and second actual usages of the oil have a rate of change of deterioration of the oil which differs from a rate of change of deterioration determined by the first and second predicted properties related to the respective first and second actual usages, wherein the difference indicates extra deterioration of the oil than deterioration predicted by the first and second predicted properties; and the second measured temperature compensated electrical property at a second actual usage of the oil has a value which exceeds a predetermined extreme value of the predicted property profile, wherein the predetermined extreme value is exceeded at a time which is earlier than a time predicted by the predicted property profile.

Figure 19:
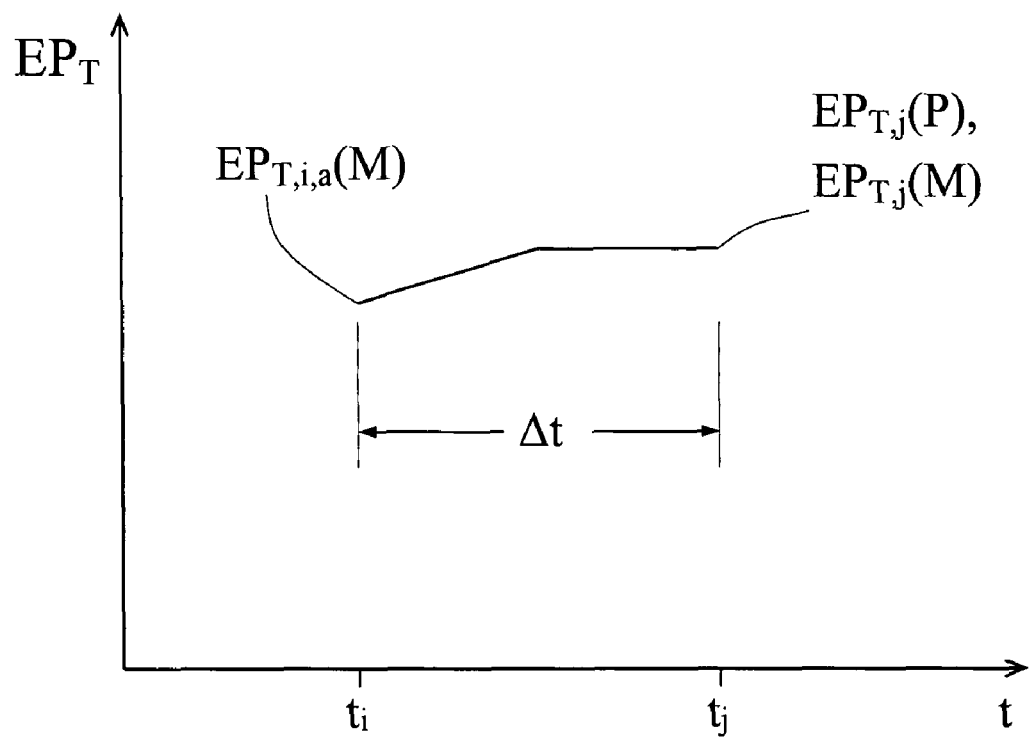
FIG. 19 is a graph showing a profile of measured temperature compensated electrical properties in a cold internal combustion engine which exhibits an initial anomaly of extra oil deterioration.

Reference to FIG. 19 illustrates a first measured temperature compensated electrical property which exhibits an initial anomaly $EP_{T,i,a}(M)$ according to a moment ($t_i$), and then returns to a value of a second predicted property $EP_{T,j}(P)$ at a second moment ($t_j$). This can occur in a first few minutes ($\Delta t$) after a cold internal combustion engine is started, wherein water has condensed into the oil before the engine is started. The presence of the condensed water causes the impedance or voltage have a value which is less than anticipated. However, after the engine has run for a short period of time, the condensed water evaporates and a second measured property $EP_{T,j}(M)$ returns to a nominal value of the second predicted property $EP_{T,j}(P)$.

In this fashion an additional embodiment for detecting the presence of water in the oil, comprises;

in step (a), providing an oil disposed in a crankcase of a cold internal combustion engine; starting the engine; observing a likely presence of the condensed water in the oil if a first measured temperature compensated electrical property exhibits an initial anomaly, which indicates extra deterioration of the oil.

The illustrations from FIGS. 16, 17, 18 and 19 disclose the abnormal oil deterioration according to an impedance or voltage measurement. It will be appreciated that if using a current measurement, curves corresponding to the abnormal oil deterioration can be derived according to the base curve in FIG. 8.

The above discloses the first preferred embodiment of the present invention methods, which applies a dual sensor configuration including the sensing capacitor immersed in the oil, and the reference capacitor immersed in the reference oil to obtain the measured temperature compensated electrical properties of the oil. Applying the dural sensor strategy the present invention enables to quantitatively obtain the measured remaining usage of the oil as $(R_M \Delta U_F)$ or $\Delta U_M$. From using the measured remaining usage of the oil, the present invention further enables to differentiate the oil deterioration which occurs in the presence or absence of water.

Figure 23:
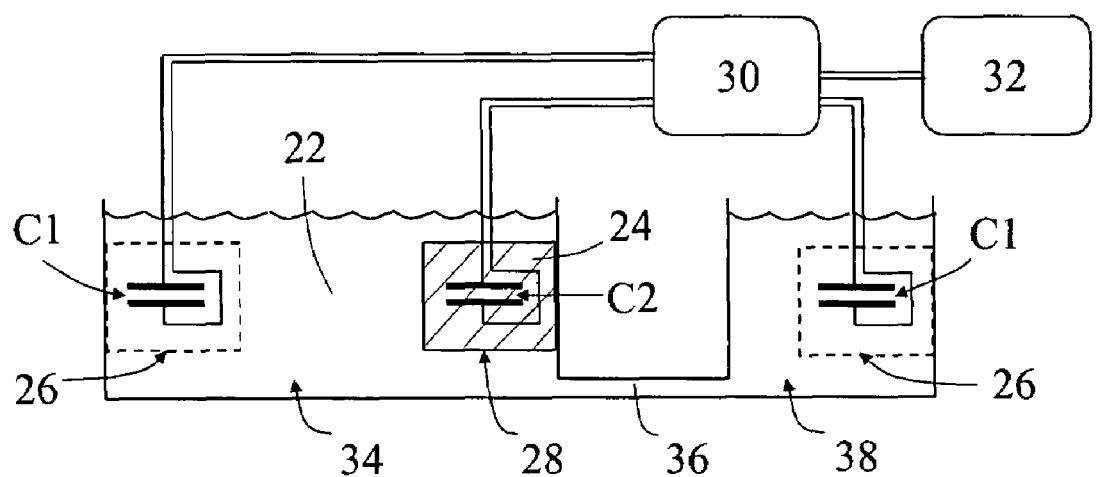
FIG. 23 is a diagram of an apparatus from a variation of the first preferred embodiment of the present invention wherein at least two measurement sensors are applied to position at the respective different locations of an oil system.

A variation of the above disclosed first preferred embodiment is comprised of at least two measurement sensors, including first and second of the respective at least two measurement sensors as illustrated in FIG. 23. They can be affixed into specific locations of an entire lubricating oil system, such as the system of a locomotive diesel engine or ship diesel engine having a separated crankcase 34 and lubricating oil reservoir 38 which are connected by oil transporting lines 36. Therefore, the varied embodiment enables to in-situ monitor if an uneven distribution of the oil deterioration occurs through the system, particularly for detecting if there would be water accumulated in the specific locations of the system. In this embodiment of the variation as illustrated in FIG. 23, each of the first and second of the respective at least two measurement sensors can be paired with one individual reference sensor, or the first and second of the respective at least two measurement sensors are combined with the same reference sensor as shown in FIG. 23. Both options enable to generate the respective two second remaining usages of the oil according to the specific locations where the first and second of the respective at least two measurement sensors are positioned. Therefore, comparing these two second remaining usages of the oil with the first predicted remaining usage for the oil, it can conclude (1) an even distribution of the normal oil deterioration in the oil system if the two second measured remaining usages of the oil are similar as compared with the first predicted remaining usage for the oil, and (2) an uneven distribution of the oil deterioration in the oil system if the two second measured remaining usages of the oil are dissimilar from each other as compared with the first predicted remaining usage for the oil.

It will be appreciated that, in that situation (2), a further analysis can be conducted on differences including among the two second measured remaining usages and from different combinations of the first predicted and one of the two second measured remaining usages. Therefore, an identification of the uneven distribution in the entire oil system is readily available and understood in accordance with the spirit and scope of the present invention methods. Therefore, such detailed analyses will not be repeated.

Figure 20:
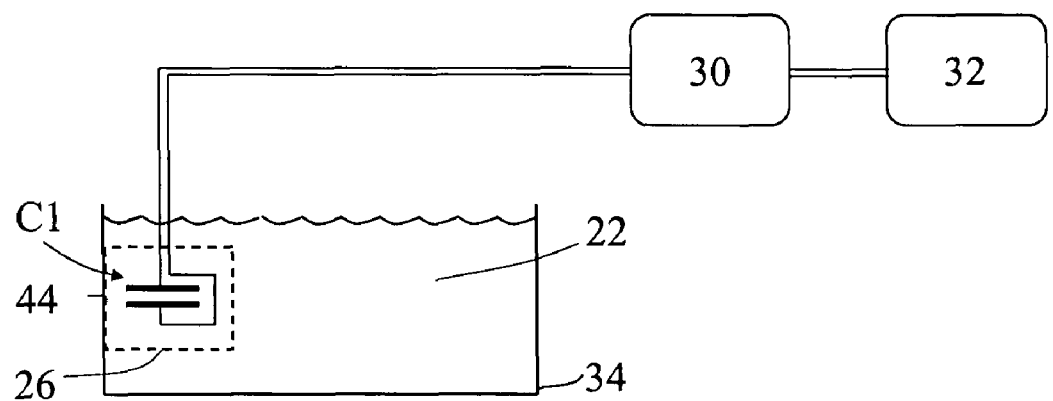
FIG. 20 is a diagram of a second apparatus of the present invention for detecting the oil deterioration and oil level.

Now referring to FIG. 20, there is illustrated a diagram of a second apparatus for detecting deterioration in oil from the present invention. This apparatus measures a measured property of the capacitor C1 in the sensor 26 to represent a measured temperature compensated electrical property $EP_T(M)$ of the oil 22. The measured property $EP_T(M)$ is temperature compensated according to the aforementioned method, or any other desired methods, such as actually measuring the temperature of the oil and applying a compensation factor to the measured property. Correspondingly, the method of the second preferred embodiment for obtaining the temperature compensated electrical property of the oil is claimed as follows:

(a) providing an oil 22 which does not contain water, the oil is disposed in an oil system of a machine such as a crankcase of an engine or a container of an electrical transformer;

(b) providing a sensor 26 which includes a capacitor (C1);

(c) positioning the sensor 26 to the oil system, wherein said capacitor (C1) is immersed in the oil;

(d) using a measuring device for measuring a first measured temperature compensated electrical property of the capacitor (C1) from a first measurement, which represents a first temperature compensated electrical property $EP_{T,i}(M)$ of the oil, wherein the first measured property of the capacitor is one of:

the impedance of the capacitor (C1);

the current passing through the capacitor (C1);

the voltage developed across the capacitor (C1);

In addition, following the above disclosed procedures which are used for obtaining the first measured temperature compensated electrical property of the oil in step "d", the second embodiment of the present invention further comprises a step (e):

(e) establishing a predicted temperature compensated electrical property profile for the oil, which represents the normal deterioration for the oil, the predicted temperature compensated property profile includes property $(EP_{T,N})$ which is equal to a measured property $EP_T(M)$ of the oil if it is unused or new and dry, and another property $(EP_{T,S})$, which is equal to a measured property $EP_T(M)$ of the oil if it is spent and dry.

Once after establishing the profile of the predicted properties $EP_T(P)$, the second preferred embodiment of the present invention can apply all the same strategies thus the same elements of the first preferred embodiment, including a second measurement, and a comparison of the second measured remaining usage and actual remaining usage in the respective two forms $(R \Delta U)$ and $(\Delta U)$ with the respective first predicted remaining usage $(R_{P,i} \Delta U_F)$ and predicted actual remaining usage. The comparison can conclude deterioration of the oil which occurs in the presence or absence of water and further confirm the second measured remaining usage which represents the actual remaining usage of the oil in the normal deterioration of the oil, in addition to obtain the deterioration ratio $(D_M)$ of the oil. Further it will be appreciated that, the second embodiment of the present invention can incorporate with the illustrations of FIGS. 16, 17, 18 and 19 for various situations where the oil deteriorates in the presence of water. However, for a purpose to reduce the length of this application, all of the same strategies, which have been disclosed in the first preferred embodiment, will not be repeated for the disclosure of the second preferred embodiment.

It will be further appreciated that the resistance and capacitive reactance are also appropriate for the second embodiment according to the spirit and scope of the present invention.

It will be another appreciated that the second preferred embodiment further enables to comprise at least two sensors, as illustrated in FIG. 23 for the first preferred embodiment, for monitoring if there is uneven distribution of the oil deterioration through the entire lubricating oil system of the machine.

II. Method for Detecting Level of an Oil

It is well known that during operation of a machine such as the internal combustion engine, lubricating oil in use will be consumed over the time which causes amount of the oil disposed in the oil system of the machine is reduced, so as to lower a top level of the oil in the oil system. When the oil amount is reduced to be lower than a predetermined threshold amount which is usually defined by a manufacturer of the machine, moving parts of the machine can not be effectively protected. Therefore, it is necessary to have a method which can on-line detect a top level of the oil in use which is reduced to the top level of a threshold amount of the oil for protecting the machine when the oil in use is reduced.

As in the case illustrated in FIG. 9 when the measurement sensor 26 is installed on the upward wall of the crankcase 34 of the internal combustion engine, the sensing capacitor (C1) is immersed in the oil 22 and is aligned with a position 44 which correlates to the top level of the threshold amount of the oil. Therefore, reduction of the amount of the oil will lower the top level of the oil in the crankcase. When the top oil level is reduced to the top level of the threshold amount of the oil, it will cause the sensing capacitor (C1) that is not fully immersed in the oil, where its lower part is immersed in the oil and upper part is filled with the air. The fact that the sensing capacitor (C1) is partially immersed in the oil will cause a change of the electrical property of the capacitor, as compared with the property when the capacitor is fully immersed in the oil. Therefore, this situation provides the present invention an opportunity to detect the top oil levels including a top level of the threshold amount of the oil by detecting abnormal electrical properties of at least two measurement sensors, which are installed according to the respective levels of the oil.

The following first illustrates a method of the present invention for detecting the top level of the threshold amount of the oil from applying the single measurement sensor, which is illustrated in FIG. 9. The method is still based on the strategy of comparing the measured remaining usage of the oil with the predicted remaining usage for the oil.

It is well known that a plate capacitor (C), for example comprising two plates in parallel, has a capacitance described as $C_p = \in S/d$, wherein ($\in$) is the dielectric constant of a dielectric medium of the capacitor; (S) is an effective area of the plates, and (d) is a distance between the plates.

Now comparing a capacitance ($C_p$) of the capacitor in two conditions, (1) if it is filled with a first dielectric medium with a dielectric constant ($\in_1$), and (2) if it is filled with a second dielectric medium with a dielectric constant ($\in_2$), it can conclude that a difference between their capacitances ($C_{P1}$) and ($C_{P2}$) is proportional to the difference of the constants ($\in_1$) and ($\in_2$).

According to the above defined conditions of the capacitances ($C_{P1}$) and ($C_{P2}$) for the same capacitor, in addition to a fact that the dielectric constant $\in$(a) of the air is substantially less (approximately 2-3 times) than the dielectric constant $\in$(o) of the oil including the mineral oil and silicon oil (this information can be found elsewhere including from the website: clippercontrol having a ".com" suffix), therefore, the capacitance ($C_{P2}$) of the capacitor filled with the air is less than the capacitance ($C_{P1}$) of the same capacitor filled with the oil. It can further conclude that, the impedance ($Z_2$) of the capacitor filled with the air is bigger than the impedance ($Z_1$) of the same capacitor filled with the oil, the voltage ($V_2$) is also bigger than the voltage ($V_i$) if the constant current measurement is applied, and the current ($I_2$) is smaller than the current ($I_1$) if a constant voltage measurement is applied.

Now comparing a capacitance ($C_p$) of the capacitor in another two situations, (1) a part of the capacitor is filled with the air and the rest of the capacitor is filled with the oil, and (2) the same capacitor is fully filled with the oil.

In the first situation when the part of the capacitor is filled with air and the rest part is filled with oil, the capacitance ($C_{P1}$) is a summation of a capacitance of the air: $C_{P1}(a) = \in(a) S_a/d$ and a capacitance of the oil: $C_{P1}(o) = \in(o) S_o/d$, wherein ($S_a$) is an effective plate area which is occupied by the air, and ($S_o$) is the area which is occupied by the oil, and $S = (S_a + S_o)$.

If comparing the capacitance ($C_{P1}$) of the capacitor filled with the air and oil in the first situation with the capacitance ($C_{P2}$) of the same capacitor fully filled with the oil in the second situation, a ratio of $C_{P1}/C_{P2}$ is equal to $[\in(a) S_a/d + \in(o) S_o/d]/\in(o)S/d$. The ratio can be simplified as: $C_{P1}/C_{P2} = [\in(a) S_a + \in(o) S_o]/\in(o)S$. Through a mathematic transformation, the simplified ratio is equal to: $1 - [\in(o) - \in(a)] S_a/S$, which has a value of less than a unity 1.

The above analysis demonstrates that the capacitance ($C_{P1}$) of the capacitor whose a part filled with the air and the rest filled with the oil is less than the capacitance ($C_{P2}$) of the same capacitor which is fully filled with the oil.

It will be appreciated that, from the above conclusion, one can derive that the impedance ($Z_1$) of the capacitor having the capacitance ($C_{P1}$) is bigger than the impedance ($Z_2$) of the same capacitor having the capacitance ($C_{P2}$). Accordingly, the voltage ($V_1$) is higher than the voltage ($V_2$) if applying a constant current measurement, and the current ($I_1$) is smaller than the current ($I_2$) if applying a constant voltage measurement. Therefore, the electrical property of the capacitor filled with the oil and air will provide a false phenomenon less deterioration of the oil, as compared with the oil deterioration determined by the same capacitor which is fully filled with the oil.

Figure 21:
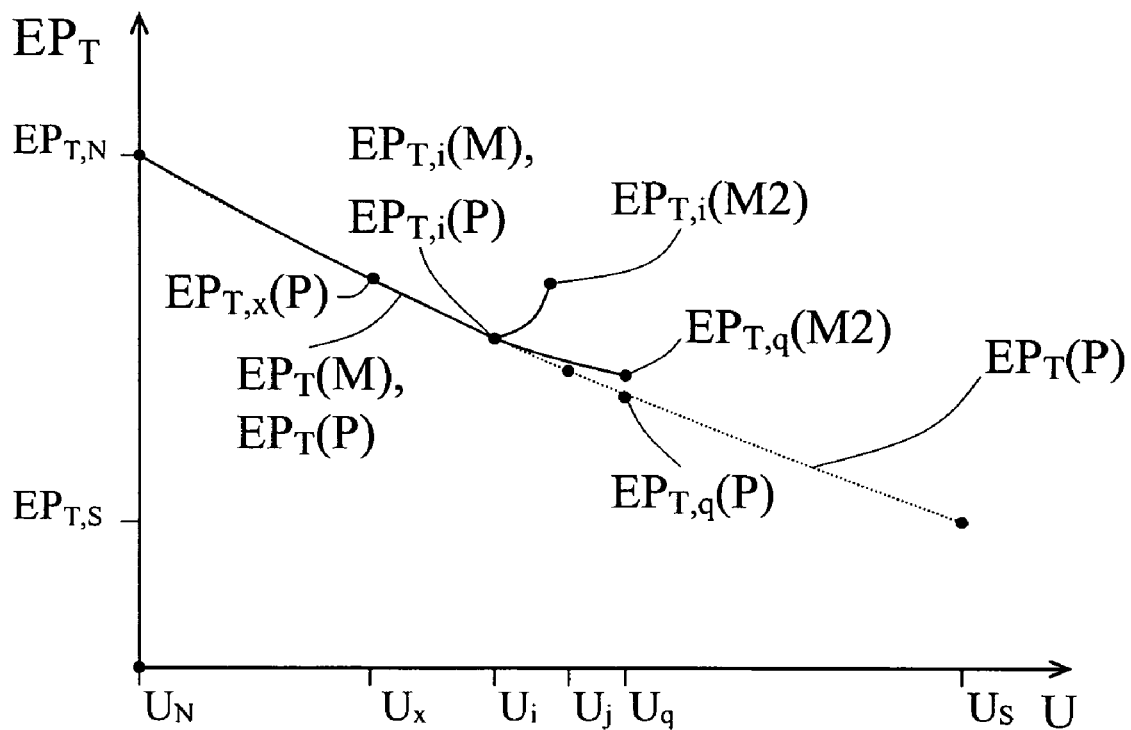
FIG. 21 is a graph which shows the same curves in FIG. 14. The difference in FIG. 21 is that the measured properties starting from the usage "$U_i$" are different from the predicted properties, which indicates less oil deterioration than it should be.
Figure 22:
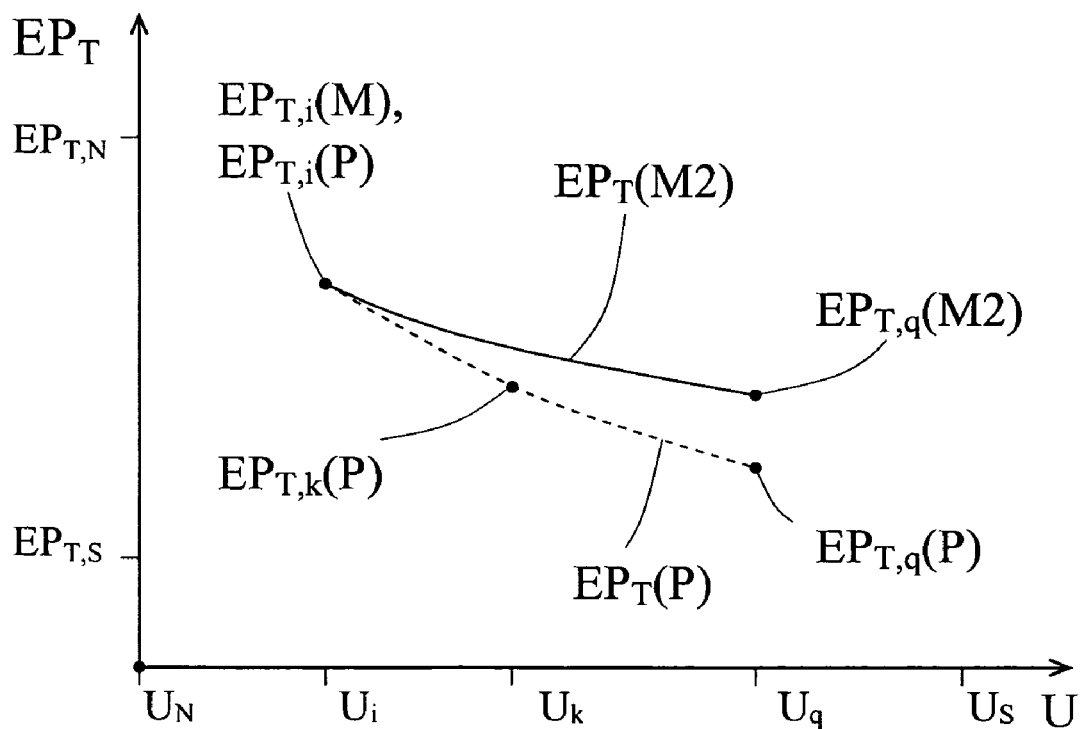
FIG. 22 is a graph which magnifies sections of the respective measured and predicted property profiles related to a range of usages from the usage $U_i$ to the usage $U_q$ of FIG. 21 according to a first situation of losing the oil.

Having the above conclusions in mind and referring to FIGS. 21 and 22 now, there is illustrated how reduction of the oil to its predetermined threshold amount causes a change of the measured temperature compensated electrical property and the remaining usage of the oil as well from the present invention. FIG. 21 illustrates a partial profile of the measured properties $EP_T(M)$, and a profile of the predicted properties $EP_T(P)$ which includes the respective properties ($EP_{T,N}$) and ($EP_{T,S}$) to correspond the respective usages ($U_N$) and ($U_S$). The predicted property profile is the same one as that illustrated in FIG. 14.

As illustrated, up to the first actual usage ($U_i$) the first measured property $EP_{T,i}(M)$ is consistent with the first predicted property $EP_{T,i}(P)$. However, staring from the first usage "$U_i$", the measured property differs from the predicted property due to the amount of the oil which is reduced to the threshold amount. Therefore, a top level of the oil is lowered to reach the top level of the predetermined threshold amount of the oil, which is aligned with the position 44, as illustrated in FIG. 9. In this situation, an upper part of the sensing capacitor (C1) is filled with the air.

It will be appreciated that there are various situations which cause the sensing capacitor that is not fully immersed in the oil. However they can be always classified to a first situation: (1) a gradually losing the oil, such as extra consumption of the oil according to an intensive usage of the machine, and a second situation: (2) a significantly losing the oil in a short period of the time, such as an oil leaking of the crankcase. Referring to FIG. 21, there are illustrated second measured properties $EP_{T,q}(M2)$ and $EP_{T,i}(M2)$ according to the respective described first and second situations (1) and (2).

As illustrated in FIG. 21, in the first situation of the gradually losing the oil, the second measured property $EP_{T,q}(M2)$ behaves a corresponding gradual departure from the profile of the predicted properties $EP_T(P)$. For example an impedance or a voltage is increasingly larger than the corresponding predicted value. In contrast, in the second situation of the quickly losing the oil, the second measured property $EP_{T,i}(M2)$ exhibits a sudden change during a small interval of the first usage ($U_i$). Accordingly, the sensing capacitor also suffers a significant loss of the oil, which makes the measured property change dramatically towards a direction of less oil deterioration. For example, the impedance or voltage exhibits a sudden and dramatic increase of the value. It will be appreciated that the first situation (1) represents the most probable situations, where occur that a top level of the oil is reduced to the top level of the predetermined threshold amount of the oil. Thus, FIG. 22 particularly illustrates the situation, from which a conclusion can be conducted for determining the predetermined threshold amount of the oil from detecting the corresponding top oil level. This conclusion can also be applied to the second situation (2).

FIG. 22 magnifies part of the profiles in FIG. 21 starting the first measured property $EP_{T,i}(M)$ at the first usage ($U_i$) from the first measurement, when the measured property $EP_T(M2)$ departs from the predicted one. After spending a short range of usages from the first usage ($U_i$) to a second usage ($U_q$), the measured property exhibits a value of the second measured property $EP_{T,q}(M2)$ at the second usage ($U_q$) from a second measurement, which is higher than a value of a second predicted property $EP_{T,q}(P)$ that represents a normal consumption of the oil according to the second usage ($U_q$). Moreover, in this situation a value of the second measured property $EP_{T,q}(M2)$ is equal to a value of a predicted property $EP_{T,k}(P)$ which correlates to an usage ($U_k$). Obviously, the usage ($U_k$) happens earlier that the second usage ($U_q$).

Therefore, the second measured property at the second usage ($U_q$) from the second measurement has a second measured remaining usage ratio, which is equal to a predicted remaining usage ratio at the usage ($U_k$): $R_{P,k}=[EP_{T,k}(P)-EP_{T,S}]/[EP_{T,N}-EP_{T,S}]$. The usage ratio ($R_{P,k}$) further determines the remaining usage $(R_{P,k}\Delta U_F)=R_{P,k}\times(U_S-U_N)$. Thus, the second measured remaining usage according to the second measured property $EP_{T,q}(M2)$ is equal to the predicted remaining usage ($R_{P,k}\Delta U_F$).

Apparently, the predicted remaining usage ratio $R_{P,k}$ is larger than a second predicted remaining usage ratio: $R_{P,q}=[EP_{T,q}(P)-EP_{T,S}]/[EP_{T,N}-EP_{T,S}]$, where the ratio ($R_{P,q}$) correlates to the physical condition having a sufficient amount of the oil that is dry in the oil reservoir, which makes the sensing capacitor (C1) fully immersed in the oil. This situation also results in that the predicted remaining usage ($R_{P,k}\Delta U_F$) is larger than a second predicted remaining usage ($R_{P,q} \Delta U_F$). Therefore, the above analysis concludes: the second measured remaining usage which is equivalent to ($R_{P,k} \Delta U_F$) is apparently larger than the second predicted remaining usage ($R_{P,q} \Delta U_F$), wherein the second predicted remaining usage represents the situation that the sensing capacitor is fully immersed in the oil whose amount is sufficient so that a top oil level is higher than the level of the predetermined threshold amount of the oil.

Consequently, a conclusion can be made according to the first situation: determining a top level of the oil which is reduced to the top level of a predetermined threshold amount of the oil if the second measured remaining usage related to the second actual usage is larger than the second predicted remaining usage according to the same second actual usage.

It will be appreciated that the above is a general conclusion for all situations including the situation (2) where the insufficient amount of the oil also happens.

It will be further appreciated that, there is an alternative way which can conduct the same conclusion regarding the first situation. Referring to FIGS. 21 and 22, there is illustrated that the second actual usage ($U_q$) corresponds to the second predicted property $EP_{T,q}(P)$. Therefore, the second predict actual remaining usage is $(\Delta U_P)=\Delta U_q=(U_S-U_q)$. However, the second measured property $EP_{T,q}(M2)$ is equal to the predicted property $EP_{T,k}(P)$, which corresponds to the actual usage ($U_k$) that is equivalent to the actual usage of the second measured property $EP_{T,q}(M2)$. Thus, the second measured actual remaining usage ($\Delta U_M$), which is equal to ($U_S-U_M$), is equivalent to the predicted actual remaining usage $\Delta U_k=(U_S-U_k)$. Apparently, the second measured actual remaining usage ($\Delta U_M$) is larger than the second predicated actual remaining usage ($\Delta U_P$). This leads to the same conclusion of reaching the top level of the predetermined threshold amount of the oil during the oil reduction if the second measured actual remaining usage is larger than the second predicted actual remaining usage. Therefore, despite of shapes of the temperature compensated electrical property profiles, the embodiment of the present invention enables to diagnose if it reaches the top level of the predetermined threshold amount of the oil during progress of the oil reduction.

In addition to application of the remaining usage of the oil, the second measured temperature compensated electrical property also can be used to predict that the top oil level is reduced to the top level of the predetermined threshold amount of the oil according to the illustrations of FIGS. 21 and 22. As illustrated in the case of the first situation (1), the second measured property $EP_{T,q}(M2)$ differs to from the second predicted property $EP_{T,q}(P)$. However, their difference indicates less oil deterioration determined by the second measured property $EP_{T,q}(M2)$ as compared with deterioration determined by the second predicted property $EP_{T,q}(P)$. Therefore, the present invention can further conclude as follows for the first situation:

predicting a top level of the oil which is reduced to the top level of the predetermined threshold amount of the oil if the second measured temperature compensated electrical property differs from the second predicted temperature compensated electrical property wherein the difference indicates less deterioration of the oil determined by the second measured temperature electrical property than deterioration determined by the second predicted temperature compensated electrical property.

Referring to FIG. 21 regarding the second situation of dramatically losing the oil the second measured property $EP_{T,i}(M2)$ is equivalent to a predicated property $EP_{T,x}(P)$ which correlates to an actual usage $U_x$. Therefore, a second measured remaining usage according to the second measured property $EP_{T,i}(M2)$ is equivalent to ($R_{P,x} \Delta U_F$), which is apparently larger that a first predicted remaining usage ($R_{P,i} \Delta U_F$) predicted by the first predicted property $EP_{T,i}(P)$. In addition, a second measured actual remaining usage ($\Delta U_M$) according to the second measured property $EP_{T,i}(M2)$ is equivalent to ($U_s-U_x$) which is also apparently larger that a first predicted actual remaining usage ($U_s-U_i$) that is predicted by the first predicted property $EP_{T,i}(P)$. From the above analysis, it can conclude a top level of the oil which is reduced to the top level of the predetermined threshold amount of the oil according to the respective judgements: (i) the second measured remaining usage is larger that the first predicted remaining usage; (ii) the second measured actual remaining usage is larger than the first predicted actual renaming usage;

and (iii) the second measured temperature compensated electrical property differs from the first predicted temperature compensated electrical property wherein the difference indicates less deterioration of the oil determined by the second measured temperature electrical property than deterioration predicted by the first predicted temperature compensated electrical property.

It will be appreciated that the illustrated curves for the electrical property in FIGS. 21 and 22 is one of the impedance or voltage. If the measured property is the current, the curve would be as that shown in FIG. 8. In addition, the electrical property could be one of the components of the impedance, resistance or reactance, rather than the total composite impedance.

Figure 24:
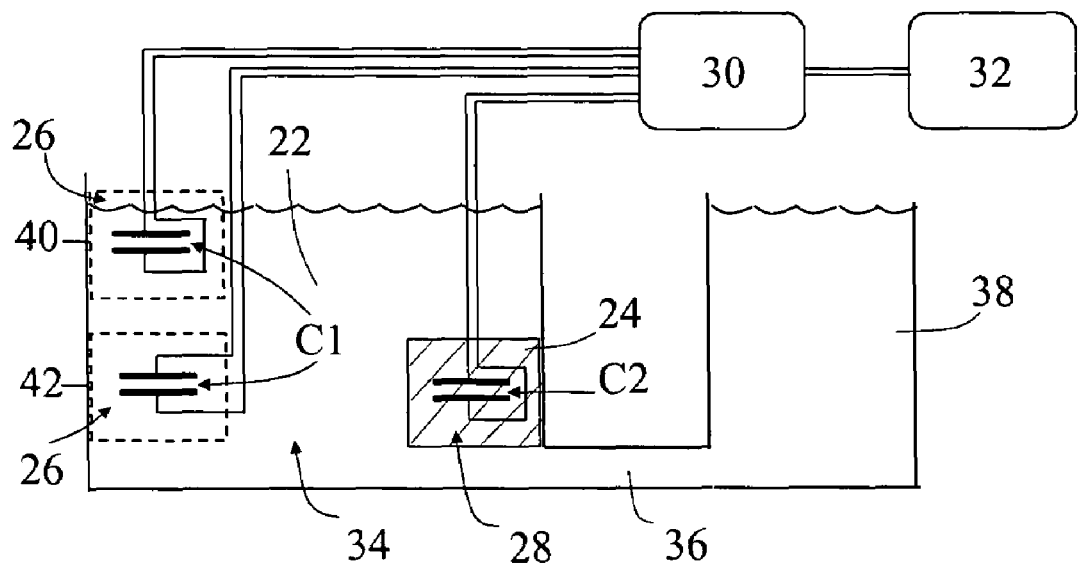
FIG. 24 is a diagram of an apparatus from another variation of the first preferred embodiment of the present invention wherein at least two measurement sensors are applied to position onto the respective different levels of an oil system.

Referring to FIG. 24, a variation of the above disclosed embodiment is to apply at least two measurement sensors 26 positioned along a vertical orientation to monitor change of a full scale of the top level of the oil in the crankcase 34. For example, in this embodiment, the first of the at least two measurement sensors is positioned onto the upward wall of the oil reservoir 34, wherein its sensing capacitor is aligned with a position 40. The position is adjacent but below the initial top level of the oil when a full amount of the oil is just newly disposed in the oil reservoir. The second of the at least two measurement sensors is installed wherein its sensing capacitor is positioned to align with the top level 42 of the predetermined threshold amount of the oil. Therefore, the capacitor of each of the respective first and second of the at least two measurement sensors will provide a respective information on change of the oil level starting an initial top level of the full amount of the oil, which then drops to the level of the predetermined threshold amount of the oil. The user of the machine can then take appropriate actions to protect the machine from damage. In addition, a third measurement sensors can also be installed to a level which is even lower as compared with the top level of the predetermined threshold amount of the oil. In this embodiment, each of the first and second of the respective at least two measurement sensors can be combined with one individual reference sensor, or the first and second of the respective at least two measurement sensors can be combined with the same one reference sensor 28 shown in FIG. 24, or several measurement sensors are combined with a reference sensor. All of these variations are within the spirit and scope of the present invention.

It will be appreciated that the above disclosed embodiment for predicting the top level of the threshold amount of the oil can also be applied to the second preferred embodiment illustrated in FIG. 20, where the sensing capacitor (C1) is aligned with the top level 44 of the threshold amount of the oil. It will be additionally appreciated that the second preferred embodiment also enables to detect change of the oil level from applying at least two sensors, which is identical to the illustration in FIG. 24 for the first preferred embodiment. Therefore, a disclosure of this embodiment will not repeated again.

It will be further appreciated that there is a very small probability that two events happen simultaneously when a large amount of the water enters into the oil and the oil significantly leaks from the reservoir. Therefore, the present invention excludes discussions of this situation which occurs in the very small probability, and which can also be classified accordingly following the spirit and scope of the present invention.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A method for detecting oil deterioration and oil level, comprising the steps of:
   a. providing an oil which does not contain water, said oil is disposed in an oil system of a machine;
   b. providing a reference oil being free of water, said reference oil is disposed in a sealed container which is located in a common temperature environment with said oil;
   c. providing a measurement sensor which includes a first capacitor;
   d. providing a reference sensor which includes a second capacitor, said second capacitor is immersed in said reference oil;
   e. positioning said measurement sensor wherein said first capacitor is immersed in said oil;
   f. using a measuring device for measuring an electrical property of said first capacitor and an electrical property of said second capacitor from a first measurement, wherein said electrical property is one of:
      an impedance of said first capacitor and an impedance of said second capacitor;
      a current passing through said first capacitor and a current passing through said second capacitor;
      a voltage developed across said first capacitor and a voltage developed across said second capacitor;
   g. combining said electrical property of said first capacitor with said electrical property of said second capacitor to obtain a first measured temperature compensated electrical property of said first capacitor, which represents a first measured property $EP_{T,i}(M)$ of said oil;
   h. following the steps (a) to (g) establishing a predicted temperature compensated electrical property profile for said oil, which represents a normal oil deterioration for said oil, said predicted temperature compensated electrical property profile includes a property $(EP_{T,N})$, which is equal to a measured property $EP_T(M)$ of said oil if it is unused or new and dry, and another property $(EP_{T,S})$, which is equal to a measured property $EP_T(M)$ of said oil if it is spent and dry;
   i. establishing a full range of usages of said oil as $\Delta U_F = (U_S - U_N)$ according to change of said properties $(EP_{T,N} - EP_{T,S})$, wherein a symbol U represents an actual usage of said oil which is an independent variable to a temperature compensated electrical property $EP_T$; said $U_N$ is an actual usage of said oil which is unused or new and dry and said $U_S$ is an actual usage of said oil which is spent and dry;
   j. defining a first measured normalized remaining usage ratio $R_{M,i}$ of said oil having said first measured property $EP_{T,i}(M)$ as: $R_{M,i} = [EP_{T,i}(M) - EP_{T,S}]/[EP_{T,N} - EP_{T,S}]$, said $R_{M,i}$ ranges from one for said oil which is new or unused and dry to zero for said oil which is spent and dry, wherein said first measured property $EP_{T,i}(M)$ correlates to a first actual usage $U_i$ of said oil and defines a first measured remaining usage of said oil as $(R_{M,i} \Delta U_F)$;
   k. from said predicted temperature compensated electrical property profile, determining a first predicted property $EP_{T,i}(P)$ according to said first actual usage as compared with said first measured property $EP_{T,i}(M)$, from which establishing a first predicated remaining usage ratio as $R_{P,i} = [EP_{T,i}(P) - EP_{T,S}]/[EP_{T,N} - EP_{T,S}]$ and a first predicted remaining usage $(R_{P,i} \Delta U_F)$ of said oil;

l. repeating steps (f) and (g) from a second measurement to obtain a second measured temperature compensated electrical property of said first capacitor which represents a second measured temperature compensated electrical property of said oil according to said first actual usage of said oil, from which obtaining a second measured remaining usage ratio and second measured remaining usage;

m. determining a normal deterioration of said oil which occurs in the absence of water if said second measured remaining usage is similar to said first predicated remaining usage ($R_{P,i} \Delta U_F$), and confirming said second measured remaining usage which represents an actual remaining usage of said oil;

n. determining an abnormal deterioration of said oil which occurs in the presence of water if said second measured remaining usage is less than said first predicted remaining usage ($R_{P,i} \Delta U_F$); and o. determining a top level of said oil which is reduced to a top level of a predetermined threshold amount of said oil if said second measured remaining usage is larger than said first predicted remaining usage ($R_{P,i} \Delta U_F$).

2. The method in accordance with claim 1, wherein said reference oil is selected from the group consisting of said unused oil, a partially spent oil, and said spent oil, and said reference oil has a similar thermal property as compared with a thermal property of said oil, is a lubricating oil and said machine is an internal combustion engine.

3. The method in accordance with claim 1 in step "d", wherein said first capacitor and second capacitor have structural relationships which make said first and second capacitors exhibit a same change of the respective electrical properties as a function of oil temperature change when said first capacitor and said second capacitor are immersed in a same oil.

4. The method in accordance with claim 1 in step "f", further comprising: said electrical property is a resistance of said first capacitor and a resistance of said second capacitor, or a capacitive reactance of said first capacitor and a capacitive reactance of said second capacitor.

5. The method in accordance with claim 1 in step "i", wherein said actual usage is a number of used times or traveled miles.

6. The method in accordance with claim 1, further comprising:

observing a likely presence of water in said oil if said second measured temperature compensated electrical property occurring any of the following:

said second measured temperature compensated electrical property exhibits a sudden change, wherein said sudden change indicates extra deterioration of said oil than deterioration predicted by said first predicted property $EP_{T,i}(P)$; and said second measured temperature compensated electrical property having a value which differs from a value of said first predicted property $EP_{T,i}(P)$, wherein said difference indicates extra deterioration of said oil than deterioration predicted by said first predicted property.

7. The method in accordance with claim 1, further comprising: disposing an oil in a cold internal combustion engine, starting said engine, and observing a likely presence of a condensed water in said oil if a measured temperature compensated electrical property exhibits an initial anomaly, wherein said initial anomaly indicates extra deterioration of said oil.

8. The method in accordance with claim 1 further comprising the following steps:

p. determining a second measured actual remaining usage of said oil as $\Delta U_M = (U_S - U_M)$, wherein said $U_M$ is corresponding with said second measured temperature compensated electrical property;

q. defining a first predicted actual remaining usage of said oil as $\Delta U_P = U_S - U_P$, wherein said $U_P$ is corresponding with said first predicted property $EP_{T,i}(P)$;

r. determining a normal deterioration of said oil which occurs in the absence of water if said second measured actual remaining usage $\Delta U_M$ is similar to said first predicted actual remaining usage $\Delta U_P$, and confirming said second measured actual remaining usage;

s. determining an abnormal deterioration of said oil which occurs in the presence of water if said second measured actual remaining usage $\Delta U_M$ is less than said first predicted actual remaining usage $\Delta U_P$; and t. determining a top level of said oil which is reduced to said top level of said predetermined threshold amount of said oil if said second measured actual remaining usage $\Delta U_M$ is larger than said first predicted actual remaining usage $\Delta U_P$.

9. The method in accordance with claim 1 in step "j", further comprising a first measured deterioration degree $D_{M,i}$ for said oil having said first measured property $EP_{T,i}(P)$ as: $D_{M,i} = [EP_{T,N} - EP_{T,i}(M)]/[EP_{T,N} - EP_{T,S}]$, wherein $D_{M,i}$ is normalized ranging from zero for said oil which is unused or new and dry to one for said oil which is spent and dry.

10. The method in accordance with claim 1 in step "e", further comprising: positioning said measurement sensor in said oil system wherein said first capacitor is positioned to align with said top level of said predetermined threshold amount of said oil of said oil system.

11. The method in accordance with claim 1, further comprising: predicting top level of said oil which is reduced to said top level of said predetermined threshold amount of said oil if said second measured temperature compensated electrical property differs from said first predicted property $E_{T,i}(P)$ wherein said difference indicates less deterioration of said oil than deterioration predicted by said first predicted property.

12. The method in accordance with claim 1, further comprising at least two said measurement sensors that include first and second of the respective at lease two measurement sensors, wherein each of which comprises a first capacitor that is immersed in said oil, said first and second of the respective at least two measurement sensors are positioned at the respective locations of said oil system of said machine, said first and second of the respective at least two measurement sensors are used which provide information regarding an even or uneven distribution of deterioration of said oil in said oil system.

13. The method in accordance with claim 12, wherein said first of said at least two measurement sensors is positioned in said oil system, its said first capacitor is positioned to align with a level adjacent but below an initial top level of said oil when a full amount of said oil is just newly disposed in said oil system, said second of said at least two measurement sensors is positioned in said oil system wherein its said first capacitor is positioned to align with said top level of said predetermined threshold amount of said oil, said first and second of the respective at least two measurement sensors are used which provide information on change of an oil level starting from a level of said full amount of said oil to said top level of said predetermined threshold amount of said oil.

14. The method in accordance with claim 1, further comprising:
   a. from a second measurement to obtain a second measured temperature compensated electrical property of said first capacitor which represents a second measured temperature compensated electrical property of said oil according to a second actual usage of said oil, from which obtaining a second measured remaining usage ratio and second measured remaining usage of said oil according to said second actual usage of said oil; from said predicted temperature compensated electrical property file obtaining a second predicted temperature compensated electrical property of said oil according to said second actual usage of said oil, from which obtaining a second predicted remaining usage ratio and second predicted remaining usage of said oil;
   b. predicting a top level of said oil which is reduced to said top level of said predetermined threshold amount of said oil if said second measured remaining usage of said oil is larger than said second predicted remaining usage of said oil;
   c. predicting a top level of said oil which is reduced to said top level of said predetermined threshold amount of said oil if said second measured actual remaining usage of said oil is larger than said second predicted actual remaining usage of said oil;
   d. predicting a top level of said oil which is reduced to said top level of said predetermined threshold amount of said oil if said second measured temperature compensated electrical property differs from said second predicted temperature compensated electrical property wherein said difference indicates less deterioration of oil than deterioration predicted by said second predicted temperature compensated electrical property;
   e. predicting a likely presence of water in said oil if said first and second measured temperature compensated electrical properties of said oil have a rate of change of deterioration of said oil which differs from a rate of change of deterioration predicted by said first and second predicted temperature compensated electrical properties of said oil, wherein said difference indicates extra deterioration of said oil than deterioration predicted by said first and second predicted temperature compensated electrical properties; and
   f. predicting a likely presence of water in said oil if said second measured temperature compensated electrical property of said oil having a value which exceeds a predetermined extreme value of said predicted temperature compensated electrical property profile, wherein said predetermined extreme value is exceeded at a usage of time which is earlier than a usage of time predicted by said predicted temperature compensated electrical property profile.

15. A method for detecting oil deterioration and oil level, comprising the steps of
   a. providing an oil which does not contain water, said oil is disposed in an oil system of a machine;
   b. providing a sensor which includes a capacitor;
   c. positioning said sensor wherein said capacitor is immersed in said oil;
   d. using a measuring device for measuring a first temperature compensated electrical property of said capacitor from a first measurement, which represents a first measured property $EP_{T,i}(M)$ of said oil, wherein said first temperature compensated electrical property of said capacitor is one of:
      an impedance of said capacitor;
      a current passing through said capacitor;
      a voltage developed across said capacitor;
   e. establishing a predicted temperature compensated electrical property profile for said oil, which resents a normal oil deterioration for said oil, said predicted temperature compensated electrical property profile includes a property ($EP_{T,N}$), which is equal to a measured property $EP_T(M)$ of said oil if it is unused or new and dry, and another property ($EP_{T,S}$), which is equal to a measured property $EP_T(M)$ of said oil if it is spent and dry;
   f. establishing a full range of usages of said oil as $\Delta U_F = (U_S - U_N)$ according to change of said properties ($EP_{T,N} - EP_{T,S}$), wherein a symbol U represents an actual usage of said oil which is an independent variable to a temperature compensated electrical property $EP_T$; said $U_N$ is an actual usage of said oil which is unused or new and dry and said $U_S$ is an actual usage of said oil which is spent and dry;
   g. defining a first measured normalized remaining usage ratio $R_{M,i}$ of said oil having said first measured property $EP_{T,i}(M)$ as: $R_{M,i} = [EP_{T,i}(M) - EP_{T,S}]/[EP_{T,N} - EP_{T,S}]$, said $R_{M,i}$ ranges from one for said oil which is new or unused and dry to zero for said oil which is spent oil and dry; wherein said first measured property $EP_{T,i}(M)$ correlates to a first actual usage $U_i$ of said oil and defines a first measured remaining usage of said oil as $(R_{M,i} \Delta U_F)$;
   h. from said predicted temperature compensated electrical property profile, determining a first predicted property $EP_{T,i}(P)$ according to said first actual usage as compared with said first measured property $EP_{T,i}(M)$, from which establishing a first predicated remaining usage ratio as $R_{P,i} = [EP_{T,i}(P) - EP_{T,S}]/[EP_{T,N} - EP_{T,S}]$ and a first predicted remaining usage $(R_{P,i} \Delta U_F)$;
   i. from a second measurement to obtain a second measured temperature compensated electrical property of said capacitor which represents a second measured temperature compensated electrical property of said oil according to said first actual usage, from which obtaining a second measured remaining usage ratio and second measured remaining usage;
   j. determining a normal deterioration of said oil which occurs in the absence of water if said second measured remaining usage is similar to said first predicated remaining usage $(R_{P,i} \Delta U_F)$, and confirming said second measured remaining usage which represents an actual remaining usage of said oil;
   k. determining an abnormal deterioration of said oil which occurs in the presence of water if said second measured remaining usage is less than said first predicted remaining usage $(R_{P,i} \Delta U_F)$; and
   l. determining a top level of said oil which is reduced to a top level of a predetermined threshold amount of said oil if said second measured remaining usage is larger than said first predicted remaining usage $(R_{P,i} \Delta U_F)$.

16. The method in accordance with claim 15 in step "d", further comprising: said temperature compensated electrical property is a resistance or a capacitive reactance of said capacitor.

17. The method in accordance with claim 15 in step "f", wherein said actual usage is a number of used times or traveled miles.

18. The method in accordance with claim 15, further comprising:
   observing a likely presence of water in said oil if said second measured temperature compensated electrical property occurring any of the following:

said second measured temperature compensated electrical property exhibits a sudden change, wherein said sudden change indicates extra deterioration of said oil than deterioration predicted by said first predicted property $EP_{T,i}(P)$; and said second measured temperature compensated electrical property having a value which differs from said first predicted property $EP_{T,i}(P)$, wherein said difference indicates extra deterioration of said oil than deterioration predicted by said first predicted property.

19. The method in accordance with claim 15, further comprising: disposing an oil in a cold internal combustion engine, starting said engine, and observing a likely presence of a condensed water in said oil if a measured temperature compensated electrical property exhibits an initial anomaly, wherein said initial anomaly indicates extra deterioration of said oil.

20. The method in accordance with claim 15, further comprising the following steps:
  m. determining a second measured actual remaining usage of said oil as $\Delta U_M=(U_S-U_M)$, wherein said $U_M$ is corresponding with said second measured temperature compensated electrical property;
  n. defining a first predicted actual remaining usage of said oil as $\Delta U_P=U_S-U_P$, wherein said $U_P$ is corresponding with said first predicted property $EP_{T,i}(P)$;
  o. determining a normal deterioration of said oil which occurs in the absence of water if said second measured actual remaining usage $\Delta U_M$ is similar to said first predicted actual remaining usage $\Delta U_P$, and confirming said second measured actual remaining usage;
  p. determining an abnormal deterioration of said oil which occurs in the presence of water if said second measured actual remaining usage $\Delta U_M$ is less than said first predicted actual remaining usage $\Delta U_P$; and
  q. determining a top level of said oil which is reduced to said top level of said predetermined threshold amount of said oil if said second measured actual remaining usage $\Delta U_M$ is larger than said first predicted actual remaining usage $\Delta U_P$.

21. The method in accordance with claim 15 in step "g", further comprising a first measured deterioration degree $D_{M,i}$ for said oil having said first measured property $EP_{T,i}(M)$ as: $D_{M,i}=[EP_{T,N}-EP_{T,i}(M)]/[EP_{T,N}-EP_{T,S}]$, wherein $D_{M,i}$ is normalized ranging from zero for said oil which is new or unused and dry to one for said oil which is spent and dry.

22. The method in accordance with claim 15 in step "c", further comprising: positioning said sensor in said oil system wherein said capacitor is positioned to align with said top level of said predetermined threshold amount of said oil in said oil system of said machine, wherein said oil is a lubricating oil and said machine is an internal combustion engine.

23. The method in accordance with claim 15, further comprising: predicting a top level of said oil which is reduced to said top level of said predetermined threshold amount of said oil if said second measured temperature compensated electrical property differs from said first predicted property $EP_{T,i}(P)$ wherein said difference indicates less deterioration of said oil than deterioration predicted by said first predicted electrical property.

24. The method in accordance with claim 15, further comprising at least two said sensors that include first and second of the respective at least two sensors, wherein each of which comprises a capacitor that is immersed in said oil, said first and second of the respective at least two sensors are positioned at the respective locations of said oil system of said machine, said first and second of the respective at least two sensors are used which provide information regarding an even or uneven distribution of deterioration of said oil in said oil system.

25. The method in accordance with claim 24, wherein said first of said at least two sensors is positioned in said oil system, its said capacitor is positioned to align with a level adjacent but below an initial top level of said oil when a full amount of said oil is just newly disposed in said oil system, said second of said at least two sensors is positioned in said oil system wherein its said capacitor is positioned to align with said top level of said predetermined threshold amount of said oil, said first and second of the respective at least two sensors are used which provide information on change of an oil level starting from a level of said full amount of said oil to said top level of said predetermined threshold amount of said oil.

26. The method in accordance with claim 15, further comprising:
  a. from a second measurement to obtain a second measured temperature compensated electrical property of said capacitor which represents a second measured temperature compensated electrical property of said oil according to a second actual usage of said oil, from which obtaining a second measured remaining usage ratio and second measured remaining usage of said oil according to said second actual usage of said oil; from said predicted temperature compensated electrical property file obtaining a second predicted temperature compensated electrical property of said oil according to said second actual usage of said oil, from which obtaining a second predicted remaining usage ratio and second predicted remaining usage of said oil;
  b. predicting a top level of said oil which is reduced to said top level of said predetermined threshold amount of said oil if said second measured remaining usage of said oil is larger than said second predicted remaining usage of said oil;
  c. predicting a top level of said oil which is reduced to said top level of said predetermined threshold amount of said oil if said second measured actual remaining usage of said oil is larger than said second predicted actual remaining usage of said oil;
  d. predicting a top level of said oil which is reduced to said top level of said predetermined threshold amount of said oil if said second measured temperature compensated electrical property differs from said second predicted temperature compensated electrical property wherein said difference indicates less deterioration of said oil than deterioration predicted by said second predicted temperature compensated electrical property;
  e. predicting a likely presence of water in said oil if said first and second measured temperature compensated electrical properties of said oil have a rate of change of deterioration of said oil which differs from a rate of change of deterioration predicted by said first and second predicted temperature compensated electrical properties of said oil, wherein said difference indicates extra deterioration of said oil than deterioration predicted by said first and second predicted temperature compensated electrical properties; and
  f. predicting a likely presence of water in said oil if said second measured temperature compensated electrical property of said oil having a value which exceeds a predetermined extreme value of said predicted temperature compensated electrical property profile, wherein said predetermined extreme value is exceeded at a usage of time which is earlier than a usage of time predicted by said predicted temperature compensated electrical property profile.

27. A method for detecting oil deterioration of an oil system of a machine including steps of applying a measurement sensor having a first capacitor immersed in an oil which does not contain water and a reference sensor having a second capacitor immersed in a reference oil being free of water; using a measuring device for measuring one electrical property of the first capacitor and one electrical property of the second capacitor from a first measurement; combining the electrical properties of respective first and second capacitors to obtain a first measured temperature compensated electrical property of the first capacitor which represents a first measured temperature compensated electrical property $EP_{T,i}(M)$ of said oil that correlates to a first actual usage of said oil; establishing a predicted temperature compensated electrical property profile including a first predicted temperature compensated electrical property $EP_{T,i}(P)$ according to said first actual usage of said oil as compared with said first measured property $EP_{T,i}(M)$; establishing a first measured remaining usage ratio which determines a first measured remaining usage of said oil, and defining a first predicted remaining usage ratio which determines a first predicted remaining usage of said oil according to said first actual usage of said oil, following the above illustrated steps conducting a second measurement to obtain a second measured temperature compensated electrical property according to said first actual usage of said oil, from which to obtain a second measured remaining usage of said oil, further comprising the steps of:

a. providing at least two measurement sensors, including a first of said at least two measurement sensors having a first capacitor immersed in said oil and a second of said at least two measurement sensors having a first capacitor immersed in said oil;

b. positioning said first and second of the respective at least two measurement sensors at the respective locations of said oil system, said first and second of the respective at least two measurement sensors obtaining the respective second measured remaining usages of said oil located at the respective locations of said oil system;

c. determining an even distribution of a normal oil deterioration of said oil which occurs in the absence of water in said oil system if said second measured remaining usages from the respective first and second of the respective at least two measurement sensors are similar to said first predicted remaining usage of said oil, and confirming one of said second measured remaining usages as an actual remaining usage of said oil in said oil system; and d. determining an uneven distribution of oil deterioration in said oil system if said second measured remaining usages form the respective first and second of said at least two measurement sensors are different from each other, as compared with said first predicted remaining usage.

28. The method in accordance with claim 27, wherein said oil is a lubricating oil which is disposed in an oil system of an internal combustion engine.

* * * * *